(12) United States Patent
Baker

(10) Patent No.: US 11,804,308 B2
(45) Date of Patent: Oct. 31, 2023

(54) PATHWAY PLANNING SYSTEM AND METHOD

(71) Applicant: COVIDIEN LP, Mansfield, MA (US)

(72) Inventor: Matt W. Baker, Edina, MN (US)

(73) Assignee: Covidien LP, Mansfield, MA (US)

( * ) Notice: Subject to any disclaimer, the term of this patent is extended or adjusted under 35 U.S.C. 154(b) by 53 days.

(21) Appl. No.: 17/520,460

(22) Filed: Nov. 5, 2021

(65) Prior Publication Data

US 2022/0059237 A1    Feb. 24, 2022

Related U.S. Application Data

(63) Continuation of application No. 15/436,323, filed on Feb. 17, 2017, now Pat. No. 11,200,983, which is a
(Continued)

(51) Int. Cl.
*G06F 3/048* (2013.01)
*G16H 50/50* (2018.01)
(Continued)

(52) U.S. Cl.
CPC .......... *G16H 50/50* (2018.01); *G06F 3/0482* (2013.01); *G06F 3/04845* (2013.01);
(Continued)

(58) Field of Classification Search
None
See application file for complete search history.

(56) References Cited

U.S. PATENT DOCUMENTS

| 5,611,025 A | 3/1997 | Lorensen et al. |
| 5,971,767 A | 10/1999 | Kaufman et al. |

(Continued)

FOREIGN PATENT DOCUMENTS

| CN | 1874717 A | 12/2006 |
| CN | 102422335 A | 4/2012 |

(Continued)

OTHER PUBLICATIONS

Analyze Direct, Inc "Analyze 10.0 Essential Training Guide", Jan. 1, 2010, XP055532639, [Retrieved from the Internet on Dec. 11, 2018].

(Continued)

*Primary Examiner* — William C Trapanese
(74) *Attorney, Agent, or Firm* — WEBER ROSSELLI & CANNON LLP

(57) ABSTRACT

A system and method for planning a pathway through an anatomical luminal network of a patient including a computing device having at least one processor; a display device in communication with the computing device; and a user interface configured for display on the display device and configured to guide a user through a pathway planning procedure. The user interface includes a patient selection window configured to receive a user input to select a patient having CT image data on which to perform pathway planning; a target selection window configured to receive a user input to select at least one target from the CT image data; and an airway finder window configured to generate at least one pathway from the at least one target to an entry point of the anatomical luminal network in response to a user input.

20 Claims, 23 Drawing Sheets

Related U.S. Application Data continuation of application No. 13/839,224, filed on Mar. 15, 2013, now Pat. No. 9,639,666.

(51) Int. Cl.
| | |
|---|---|
| *G16H 40/63* | (2018.01) |
| *G06F 3/0482* | (2013.01) |
| *G06F 3/04845* | (2022.01) |
| *G06T 15/08* | (2011.01) |
| *G06T 19/00* | (2011.01) |

(52) U.S. Cl.
CPC ............ *G06T 15/08* (2013.01); *G06T 19/003* (2013.01); *G16H 40/63* (2018.01); *G06T 2200/24* (2013.01); *G06T 2210/41* (2013.01)

(56) References Cited

U.S. PATENT DOCUMENTS

| | | | |
|---|---|---|---|
| 6,332,089 B1 | 12/2001 | Acker et al. | |
| 6,501,848 B1 | 12/2002 | Carroll et al. | |
| 6,505,065 B1 | 1/2003 | Yanof et al. | |
| 6,526,162 B2 | 2/2003 | Asano et al. | |
| 6,754,374 B1 | 6/2004 | Miller et al. | |
| 6,829,379 B1 | 12/2004 | Knoplioch et al. | |
| 6,901,277 B2 | 5/2005 | Kaufman et al. | |
| 6,909,913 B2 | 6/2005 | Vining | |
| 7,072,501 B2 | 7/2006 | Wood et al. | |
| 7,130,457 B2 | 10/2006 | Kaufman et al. | |
| 7,149,564 B2 | 12/2006 | Vining et al. | |
| 7,179,220 B2 | 2/2007 | Kukuk | |
| 7,233,820 B2 | 6/2007 | Gilboa | |
| 7,517,320 B2 | 4/2009 | Wibowo et al. | |
| 7,518,619 B2 | 4/2009 | Stoval et al. | |
| 7,822,461 B2 | 10/2010 | Geiger et al. | |
| 7,901,348 B2 | 3/2011 | Soper et al. | |
| 7,929,014 B2 | 4/2011 | Akimoto et al. | |
| 7,985,187 B2 | 7/2011 | Wibowo et al. | |
| 8,049,777 B2 | 11/2011 | Akimoto et al. | |
| 8,199,984 B2 | 6/2012 | Mori et al. | |
| 8,208,708 B2 | 6/2012 | Homan et al. | |
| 8,218,846 B2 | 7/2012 | Trumer et al. | |
| 8,289,316 B1 | 10/2012 | Reisman et al. | |
| 8,417,009 B2 | 4/2013 | Mizuno | |
| 8,548,778 B1 | 10/2013 | Hart et al. | |
| 8,601,385 B2 | 12/2013 | Natanzon et al. | |
| 9,639,666 B2 | 5/2017 | Baker et al. | |
| 2002/0028006 A1 | 3/2002 | Novak et al. | |
| 2004/0249267 A1 | 12/2004 | Gilboa | |
| 2005/0020911 A1 | 1/2005 | Viswanathan et al. | |
| 2005/0122343 A1 | 6/2005 | Bailey et al. | |
| 2006/0008138 A1 | 1/2006 | Zhou et al. | |
| 2006/0184016 A1 | 8/2006 | Glossop et al. | |
| 2006/0274885 A1 | 12/2006 | Wang et al. | |
| 2007/0003124 A1 | 1/2007 | Wood et al. | |
| 2007/0092864 A1 | 4/2007 | Reinhardt et al. | |
| 2007/0167801 A1 | 7/2007 | Webler et al. | |
| 2008/0027356 A1 | 1/2008 | Chen et al. | |
| 2008/0118135 A1 | 5/2008 | Averbuch et al. | |
| 2008/0183073 A1 | 7/2008 | Higgins et al. | |
| 2009/0019400 A1 | 1/2009 | Matsumoto | |
| 2009/0052754 A1 | 2/2009 | Goto et al. | |
| 2009/0209817 A1 | 8/2009 | Averbuch et al. | |
| 2009/0257550 A1 | 10/2009 | Moriya | |
| 2010/0008555 A1 | 1/2010 | Trumer et al. | |
| 2010/0135561 A1 | 6/2010 | Moulik | |
| 2010/0310146 A1 | 12/2010 | Higgins et al. | |
| 2011/0107270 A1 | 5/2011 | Wang et al. | |
| 2011/0172562 A1 | 7/2011 | Sahasrabudhe et al. | |
| 2012/0081362 A1* | 4/2012 | Kiraly ................... | A61B 6/032 345/419 |
| 2012/0105436 A1 | 5/2012 | Averbuch | |
| 2012/0203065 A1 | 8/2012 | Higgins et al. | |
| 2012/0207365 A1 | 8/2012 | Verstraeten et al. | |
| 2012/0249546 A1* | 10/2012 | Tschirren ................ | G06T 19/00 345/419 |
| 2012/0281903 A1 | 11/2012 | Trumer et al. | |
| 2012/0287238 A1 | 11/2012 | Onishi et al. | |
| 2012/0290976 A1 | 11/2012 | Lahm et al. | |
| 2013/0088512 A1 | 4/2013 | Suzuki et al. | |
| 2013/0208955 A1 | 8/2013 | Zhao et al. | |
| 2013/0223702 A1 | 8/2013 | Holsing et al. | |
| 2014/0072191 A1 | 3/2014 | Liang et al. | |
| 2014/0081129 A1 | 3/2014 | Lu et al. | |
| 2014/0228614 A1 | 8/2014 | Stopek et al. | |
| 2014/0275952 A1 | 9/2014 | Monroe et al. | |
| 2014/0282008 A1 | 9/2014 | Verard et al. | |
| 2014/0344742 A1 | 11/2014 | Wiemker et al. | |
| 2015/0012011 A1 | 1/2015 | Trovato | |

FOREIGN PATENT DOCUMENTS

| | | |
|---|---|---|
| CN | 102470014 A | 5/2012 |
| CN | 102740755 A | 10/2012 |
| EP | 1442715 A2 | 8/2004 |
| EP | 1681012 A1 | 7/2006 |
| JP | H067342 A | 1/1994 |
| JP | H06337920 A | 12/1994 |
| JP | H08166995 A | 6/1996 |
| JP | 2001087228 A | 4/2001 |
| JP | 2004105256 A | 4/2004 |
| JP | 2006116318 A | 5/2006 |
| JP | 2006127046 A | 5/2006 |
| JP | 2006192151 A | 7/2006 |
| JP | 2006255193 A | 9/2006 |
| JP | 2008173159 A | 7/2008 |
| JP | 2009247817 A | 10/2009 |
| JP | 2010510815 A | 4/2010 |
| JP | 2011092405 A | 5/2011 |
| JP | 2011125568 A | 6/2011 |
| WO | 2009016927 A1 | 2/2009 |
| WO | 2009103046 A2 | 8/2009 |
| WO | 2009138871 A2 | 11/2009 |
| WO | 2012153249 A2 | 11/2012 |
| WO | 2013080131 A1 | 6/2013 |

OTHER PUBLICATIONS

Australian Examination Report issued in application No. 2014201317 dated Mar. 5, 2018.
Australian Examination Report issued in corresponding Appl. No. AU 2018233028 dated Jun. 5, 2019 (3 pages).
Canadian Office Action issued in corresponding Appl. No. CA 2,846,215 dated Mar. 3, 2020 (6 pages).
Chinese Office Action issued in application No. 201410093840.7 dated Mar. 19, 2018.
Chinese Office Action issued in application No. 201410095041.3 dated Dec. 11, 2017 with translation.
Chinese Office Action issued in Chinese Patent Application No. 201410093840.7 dated Sep. 4, 2017 with translation.
Chinese Office Action issued in corresponding Appl. No. CN 201410093840.7 dated Jul. 3, 2019, together with English language translation (19 pages).
Chinese Office Action issued in corresponding Chinese application No. 201410093834.1 dated Aug. 9, 2017 with translation, pp. 1-24.
Decision of Rejection issued in corresponding Appl. No. JP 2014-048406 dated Dec. 11, 2018, together with English language translation (6 pages).
EP Examination Report for EP 14 160 219.3 dated Feb. 15, 2017.
European Examination Report issued in corresponding EP Appl. No. 18203503.0 dated Feb. 22, 2021 (8 pages).
European Office Action for EP 14 160 217.7 dated Nov. 15, 2016.
European Office Action for European Appln. No. 14 160 220.1 dated Nov. 24, 2016.
European Search Report for EP 14 16 0217 dated Jul. 29, 2014.
Extended European Search Report dated Jul. 31, 2014 for EP 14 16 0219.
Extended European Search Report issued in corresponding Appl. No. EP 18203503.0-1217 dated Dec. 18, 2019 (8 pages).
Graham et al., Computer-Based Route-Definition System for Peripheral Bronchoscopy, Journal of Digital Imaging, vol. 25, No. 2 (2011).

(56) References Cited

OTHER PUBLICATIONS

Japanese Office Action issued in application No. 2014-048406 dated Dec. 19, 2017 with translation.
Japanese Office Action issued in application No. 2014-048407 dated Nov. 28, 2017 with translation.
Japanese Office Action issued in application No. 2014-048579 dated Jan. 9, 2018 with translation.
Japanese Office Action issued in Application No. 2014-048579, dated Sep. 25, 2018 with translation (18 pages).
Japanese Office Action issued in corresponding Appl. No. JP 2018-132261 dated Jul. 30, 2019, together with English language translation (15 pages).
Japanese Office Action issued in JP Application No. 2014-048406, dated Aug. 28, 2018.
Khan et al.. Safety of Pacemakers and Defibrillators in Electromagnetic Navigation Bronchoscopy, Chest, vol. 143, No. 1, p. 75 (Jan. 2013).
Leong et al., Electromagnetic navigation bronchoscopy, Journal of thoracic disease, vol. 4, No. 2, pp. 173-185 (Apr. 2012).
Michael W. Graham et al., "Robust System for Human Airway-Tree Segmentation", Proc. of SPIE, vol. 6914, Mar. 6, 2008, p. 69141J-1-69141J-18.
Office Action issued in corresponding Chinese Appl. No. CN 201410093840.7 dated Jun. 3, 2020 (8 pages) together with English language translation (12 pages).
Office Action issued in corresponding Chinese Application No. 201810597159 4 dated Apr. 1, 2021 together with English language translation retrieved from the Global Dossier (25 pages).
Office Action issued in corresponding Japanese Appl. No. JP 2019-058035 dated May 14, 2019, together with English language translation (7 pages).
SuperDimension: superDimension's iLogic Promotional Video, www/youtube.com/watch?v=3oCkvD8eaMQ (Jun. 2010), retrieved on Jul. 22, 2014.
Xu, Sheng et al., "3D motion tracking of pulmonary lesions using CT fluoroscopy images for robotically assisted lung biopsy", SPIE Medical Imaging 2004 proceedings, May 2004, pp. 1-9.
Chinese Office Action issued in Chinese Patent Application No. 201810597159.4 dated Jan. 11, 2022. English translation not available.
Summons to attend oral proceedings pursuant to Rule 115(1) EPC issued in European Patent Application No. 18203503.0 dated Nov. 15, 2022, 13 pages.

* cited by examiner

PATHWAY PLANNING SYSTEM AND METHOD

CROSS-REFERENCE TO RELATED APPLICATIONS

This application is a continuation of U.S. patent application Ser. No. 13/839,224 filed on Mar. 15, 2013, the entire contents of which are incorporated by reference herein for all purposes.

BACKGROUND

Technical Field

The present disclosure relates to a system and method for planning a pathway through an anatomical luminal network of a patient.

Discussion of Related Art

During a surgical procedure clinicians often use CT images for determining a plan or pathway for navigating through the luminal network of a patient. It is often difficult, however, for the clinician to effectively plan a pathway based on CT images alone, especially in the smaller branches of the bronchial tree where CT images typically do not provide sufficient resolution for accurate navigation.

To assist a clinician in planning a pathway through a luminal network, automated pathway planning systems and methods have been implemented that automatically generate a pathway from a target designated on a CT image to the an entry point of a patient, e.g., a patient's mouth, nose, other natural entry points or an artificial entry point such, for example, as an incision. One example of an automated pathway planning system and method can be found in U.S. Pat. No. 8,218,846, the entirety of which is incorporated herein by reference.

When using a fully automated pathway planning system, however, the medical device may reach the end of the pathway in an orientation where the working end of the medical device is not oriented toward the target. In this example, a side of the medical device may be oriented towards the target instead of the working end and it may be difficult or impossible for the clinician to gain access to the target with the working end. In particular, when navigating through the small airways of the bronchial tree it may be difficult or even impossible to flex or turn the working end of the medical device towards a target when the target is located perpendicular to the path of travel of the medical device through the small airways.

SUMMARY

Systems and methods for planning a pathway through an anatomical luminal network of a patient are provided.

In an aspect of the present disclosure, a system for planning a pathway through an anatomical luminal network of a patient is disclosed including a computing device including at least one processor; a display device in communication with the computing device; a user interface configured for display on the display device and configured to guide a user through a pathway planning procedure. The user interface includes a patient selection window configured to receive a user input to select a patient having CT image data on which to perform pathway planning; a target selection window configured to receive a user input to select at least one target from the CT image data; and an airway finder window configured to generate at least one pathway from the at least one target to an entry point of the anatomical luminal network in response to a user input.

In an aspect of the present disclosure, the patient selection window is configured to import patients and CT image data from at least one memory device associated with the computing device.

In an aspect of the present disclosure, the at least one processor is configured to generate a three-dimensional CT volume from the CT image data selected by the user.

In an aspect of the present disclosure, the at least one processor is configured to generate a three-dimensional model of the patient's bronchial tree from the CT image data selected by the user for displaying on the display.

In an aspect of the present disclosure, the target selection window includes: a CT image window configured to display a slice of the CT image data; a localizer window configured to display an image of at least one lung, the localizer window including a localizer configured to identify a location of the displayed slice relative to the at least one lung; and a target selection element configured to select the target from a displayed slice of CT image data in response to a user input.

In an aspect of the present disclosure, the CT image window is configured to display at least one other slice of the CT image data in response to a user input and the localizer is configured to move relative to the image of the at least one lung to identify the location of the displayed at least one other slice relative to the at least one lung.

In an aspect of the present disclosure, the airway finder window is configured to display a CT image including the selected at least one target, the CT image rotatable about a pre-defined axis to assist the user in identifying an airway of the anatomical luminal network.

In an aspect of the present disclosure, the pre-defined axis is an axis defined from the target to a known airway of the anatomical luminal network.

In an aspect of the present disclosure, the pre-defined axis is an axis defined from the target to a portion of a trachea in the anatomical luminal network.

In an aspect of the present disclosure, the pre-defined axis is an axis defined by a pathway from the target to a waypoint.

In an aspect of the present disclosure, the pre-defined axis is an axis defined by a pathway from a first waypoint to a second waypoint.

In an aspect of the present disclosure, the airway finder window further includes a rotation interface configured to identify an amount of rotation of the CT image about the pre-defined axis relative to an initial rotational orientation of the CT image.

In an aspect of the present disclosure, a method for planning a pathway through an anatomical luminal network of a patient is disclosed including the steps of: importing CT image data of a patient selected by a user input; generating a three-dimensional CT volume from the CT image data; displaying a slice of the three-dimensional CT volume; receiving a user input identifying a target; defining an axis of rotation from the identified target to a known airway of the three-dimensional CT volume; rotating a slice of the three-dimensional CT volume about the axis of rotation; receiving an input from a user indicating a location for a new waypoint in an airway of the rotated slice; setting a first waypoint in the identified airway; and generating a first pathway from the target to the first waypoint.

In an aspect of the present disclosure, the method further includes the steps of: determining if the first waypoint is located in a known airway of the three-dimensional CT volume; and automatically completing a pathway from the first waypoint to the entry point if the first waypoint is located in a known airway.

In an aspect of the present disclosure, the method further includes the steps of: defining the axis of rotation along the first pathway; rotating a slice of the three-dimensional CT volume about the axis of rotation; receiving an input from a user indicating a location for a new waypoint in an airway of the rotated slice; setting a second waypoint in the identified airway; and generating a second pathway from the first waypoint to the second waypoint.

In an aspect of the present disclosure, the method further includes the steps of: determining if the second waypoint is located in a known airway of the three-dimensional CT volume; and automatically completing a pathway from the second waypoint to the entry point if the second waypoint is located in a known airway.

In an aspect of the present disclosure, a non-transitory computer-readable storage medium encoded with a program is disclosed, that, when executed by a processor causes a user interface to perform the steps of: importing CT image data of a patient selected by a user input; generating a three-dimensional CT volume from the CT image data; displaying a slice of the three-dimensional CT volume; receiving a user input identifying a target; defining an axis of rotation from the identified target to a known airway of the three-dimensional CT volume; rotating a slice of the three-dimensional CT volume about the axis of rotation; receiving an input from a user indicating a location for a new waypoint in an airway of the rotated slice; setting a first waypoint in the identified airway; and generating a first pathway from the target to the first waypoint.

In an aspect of the present disclosure, the program further causes the user interface to perform the steps of: determining if the first waypoint is located in a known airway of the three-dimensional CT volume; and automatically completing a pathway from the first waypoint to the entry point if the first waypoint is located in a known airway.

In an aspect of the present disclosure, the program further causes the user interface to perform the steps of: defining the axis of rotation along the first pathway; rotating a slice of the three-dimensional CT volume about the axis of rotation; receiving an input from a user indicating a location for a new waypoint in an airway of the rotated slice; setting a second waypoint in the identified airway; and generating a second pathway from the first waypoint to the second waypoint.

In an aspect of the present disclosure, the program further causes the user interface to perform the steps of: determining if the second waypoint is located in a known airway of the three-dimensional CT volume; and automatically completing a pathway from the second waypoint to the entry point if the second waypoint is located in a known airway.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which.

DETAILED DESCRIPTION

Although the present disclosure will be described in terms of a specific embodiment, it will be readily apparent to those skilled in this art that various modifications, rearrangements and substitutions may be made without departing from the spirit of the present disclosure. The scope of the present disclosure is defined by the claims appended hereto.

Figure 1:
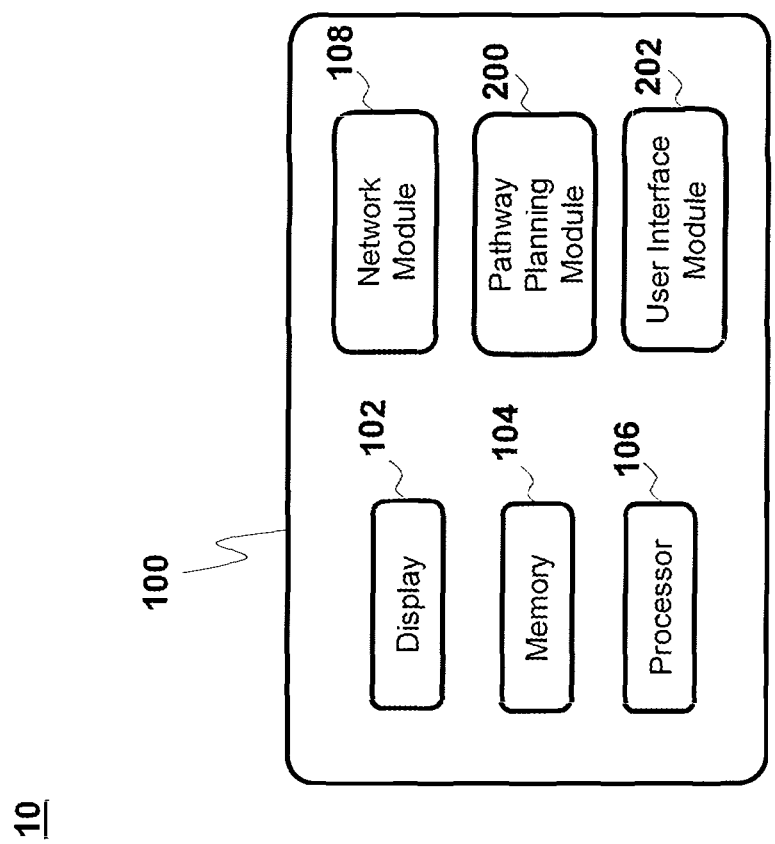
FIG. 1 is a schematic diagram of a computing device for pathway planning in accordance with an embodiment of the present disclosure.

Referring now to FIG. 1, the present disclosure is generally directed to a pathway planning system 10 and method for planning a pathway through an anatomical luminal network of a patient for use during an operation. The pathway planning system 10 may include a computing device 100 such as, for example, a laptop, desktop, tablet, or other similar device, having a display 102, memory 104, one or more processors 106 and/or other components of the type typically found in a computing device. Display 102 may be touch sensitive and/or voice activated, enabling display 102 to serve as both an input and output device. Alternatively, a keyboard (not shown), mouse (not shown), or other data input devices may be employed.

Memory 104 includes any non-transitory, computer-readable storage media for storing data and/or software that is executable by processor 106 and which controls the operation of the computing device 100. In an embodiment, the memory 104 may include one or more solid-state storage devices such as flash memory chips. In an alternative embodiment, the memory 104 may be mass storage connected to the processor 106 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 106. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computing device 100.

Computing device 100 may also include a network module 108 connected to a distributed network or the internet via a wired or wireless connection for the transmission and reception of data to and from other sources. For example, computing device 100 may receive computed tomographic (CT) images of a patient from a server, for example, a hospital server, interest server, or other similar servers, for use during pathway planning. Patient CT images may also be provided to computing device 100 via a removable memory 104.

A pathway planning module 200 includes a software program stored in memory 104 and executed by processor 106 of the computing device 100. As will be described in more detail below, pathway planning module 200 guides a clinician through a series of steps to develop a pathway plan for later use during a medical procedure. Pathway planning module 200 communicates with a user interface module 202 for displaying visual interactive features to a clinician on the display 102 and for receiving clinician input.

As used herein, the term "clinician" refers to any medical professional (i.e., doctor, surgeon, nurse, or the like) or other user of the pathway planning system 10 involved in planning, performing, monitoring and/or supervising a medical procedure involving the use of the embodiments described herein.

Figure 2A:
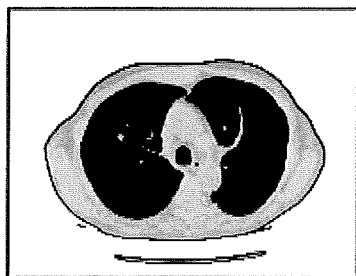
FIG. 2A is a view of a CT scan image of a patient's lungs taken from the Axial direction in accordance with an embodiment of the present disclosure.
Figure 2B:
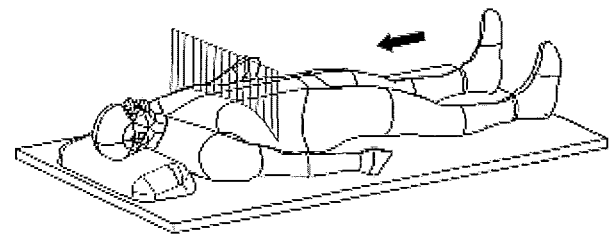
FIG. 2B is perspective view a patient's body illustrating the Axial direction in accordance with an embodiment of the present disclosure.
Figure 2C:
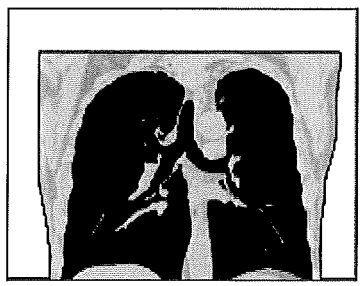
FIG. 2C is a view of a CT scan image of a patient's lungs taken from the Coronal direction in accordance with an embodiment of the present disclosure.
Figure 2D:
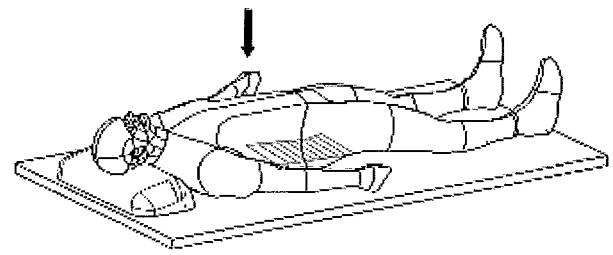
FIG. 2D is perspective view of a patient's body illustrating the Coronal direction in accordance with an embodiment of the present disclosure.
Figure 2E:
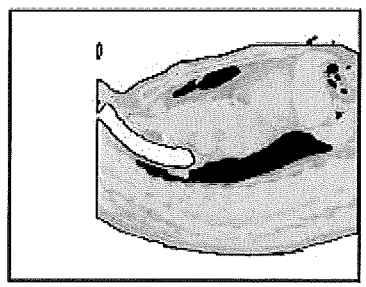
FIG. 2E is a view of a CT scan image of a patient's lungs taken from the Sagittal direction in accordance with an embodiment of the present disclosure.
Figure 2F:
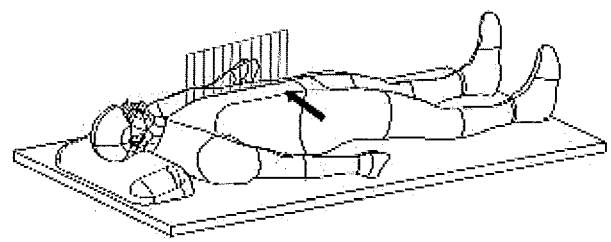
FIG. 2F is perspective view of a patient's body illustrating the Sagittal direction in accordance with an embodiment of the present disclosure.

Referring temporarily to FIGS. 2A-2F, as a practical matter the most effective method of identifying targets involves the use of a computed tomographic (CT) image. By way of introduction, the use of CT images as a diagnostic tool has become routine and CT results are frequently the primary source of information available to a clinician regarding the size and location of a lesion, tumor or other similar target of interest. This information is used by the clinician for planning an operative procedure such as a biopsy, but is only available as "offline" information which must typically be memorized to the best of the practitioner's ability prior to beginning a procedure. CT images are typically obtained by digitally imaging a patient in slices in each of the Axial, Coronal and Sagittal directions. For example, FIG. 2A illustrates a slice of a CT image taken from the Axial direction, i.e., as though looking parallel to the spine of the patient as illustrated in FIG. 2B. FIG. 2C illustrates a slice of a CT image taken from the Coronal direction, i.e., from a birds eye view of the patient as illustrated in FIG. 2D. FIG. 2E illustrates a slice of a CT image taken from the Sagittal direction, i.e., from a side of the patient as illustrated in FIG. 2F. A clinician may review the CT image data slice by slice from each direction when attempting to identify or locate a target.

Figure 3:
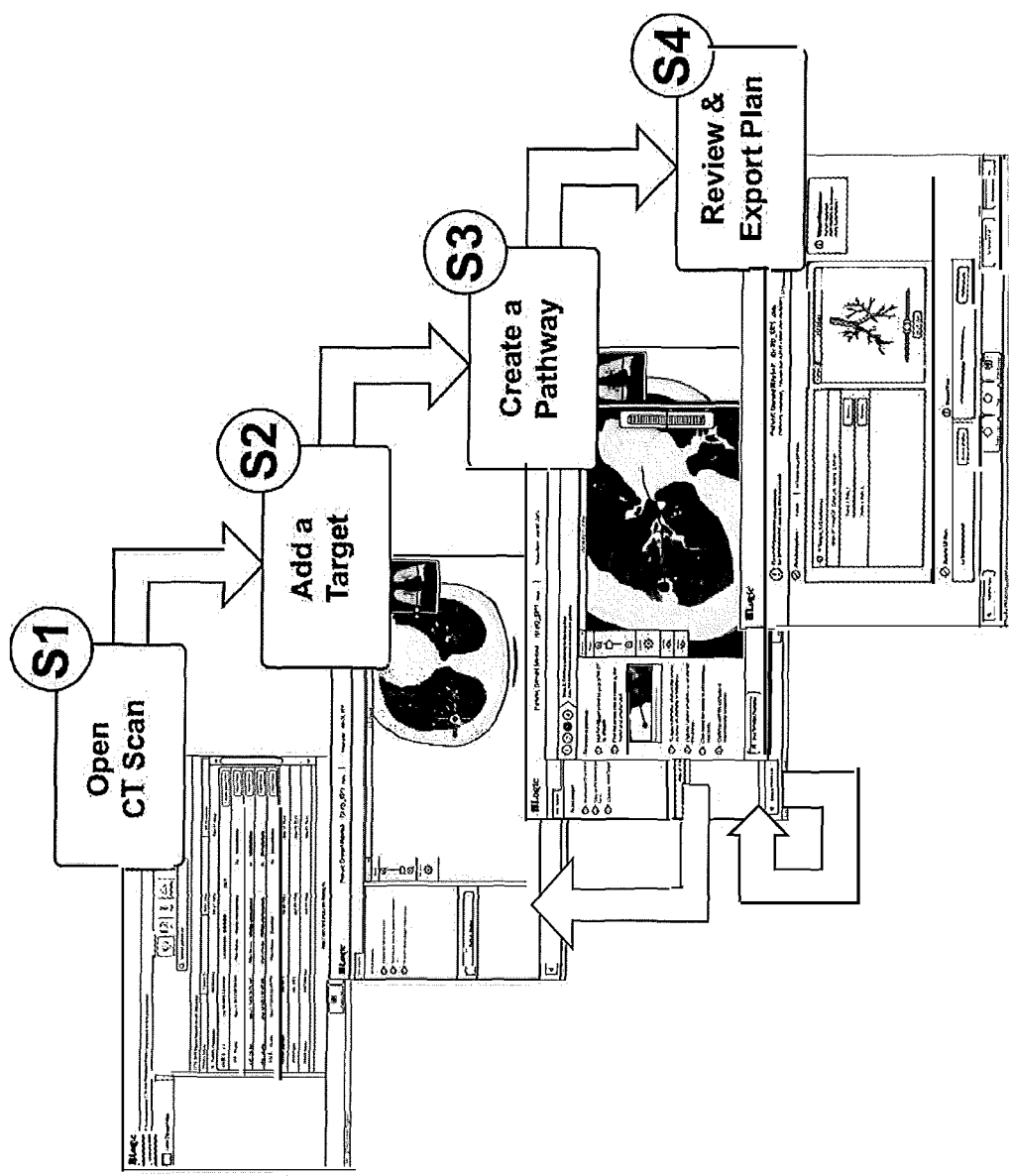
FIG. 3 is a flow chart illustrating the four phases of pathway planning in accordance with an embodiment of the present disclosure.

Referring now to FIG. 3, in an embodiment, pathway planning using the pathway planning module 200 may be performed in four separate phases. In a first phase S1, a clinician selects a patient for pathway planning. In a second phase S2, the clinician adds a target. In a third phase S3, the clinician creates the pathway to the target. Finally, in the fourth phase S4, the clinician reviews and accepts the plan and may export the plan for use in a medical procedure. The clinician may repeat either or both of the second and third phases S2 and S3 as needed to select additional targets and/or create additional pathways for a particular patient. For example, the clinician may select additional targets and may create a pathway to each target. The clinician may also or alternatively create multiple pathways the same target. With reference to FIGS. 4-16, each of stages S1-S4 will now be described in more detail below.

As used herein, the term "window" refers to any screen, image, overlay, user interface or combination thereof, projected or provided on the display 102 by user interface 202.

Figure 4:
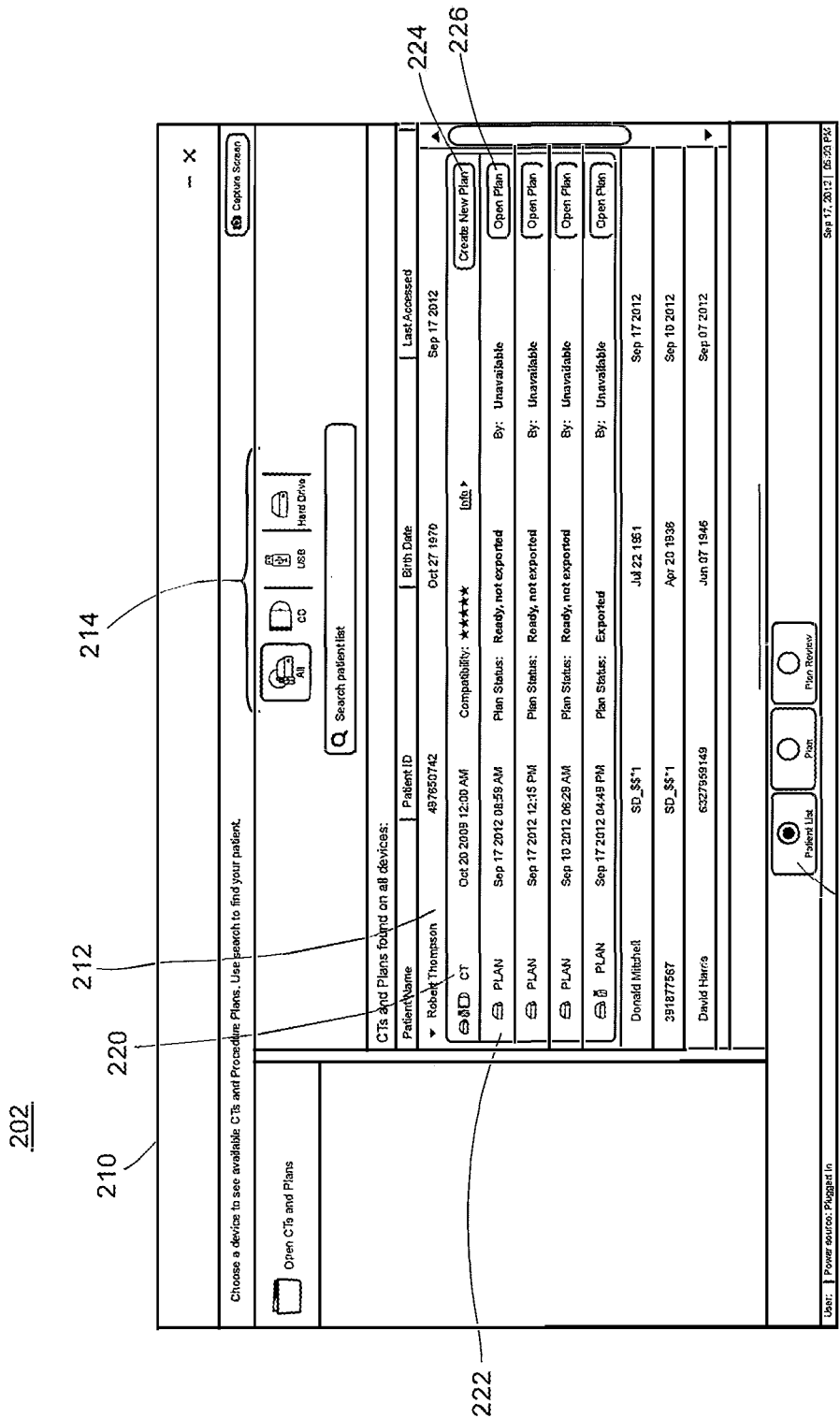
FIG. 4 is an illustration of a user interface for the selection of patient data in accordance with an embodiment of the present disclosure.
Figure 5:
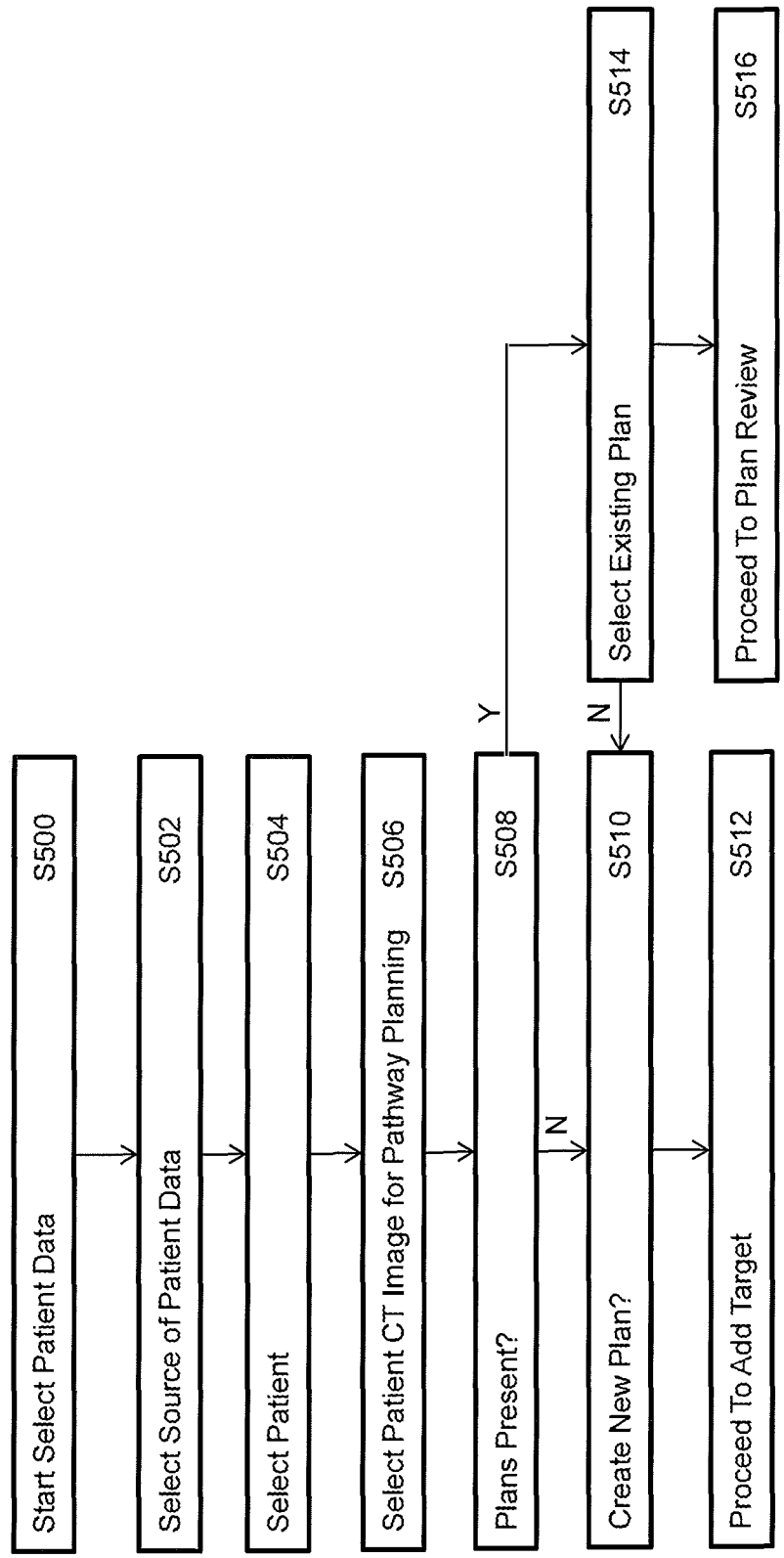
FIG. 5 is a flow chart of a method of selecting patient data in accordance with an embodiment of the present disclosure.

Referring now to FIGS. 4 and 5, in phase S1, user interface 202 presents a clinician with a window 210 for selecting patient data 212 on which to perform pathway planning. FIG. 4 illustrates user interface 202 including window 210 while FIG. 5 illustrates a method of selecting patient data according to an embodiment of the present disclosure. User interface 202 initially starts the method of selecting patient data at step S500 by opening window 210 for the clinician's review. Window 210 includes a selectable source location menu 214 that provides the clinician with the ability to select a source from which patient data 212 is received for use in pathway planning. In step S510 the clinician selects from a number of storage or memory devices including, for example, cd, dvd, blue-ray, other insertable optical media, universal serial bus (USB) memory devices, external or internal hard drives, solid state storage devices, or any other type of memory or storage 104 connected to or in data communication with computing device 100, as described above. The window 210 may also provide access to patient data 212 stored in a remote location such as, for example, a server on a network or the internet. Source location menu 214 may allow the clinician to select a single source of patient data or may allow the clinician to select multiple sources of patient data at the same time. Source location menu 214 may also include an option to list patients from all sources. In step S504, the clinician may search through the list of patients or may input a search term in a search box 216 to narrow down the list of patients to those meeting a selected criteria such as, for example, a patient's first or last name, ID number, date of birth or other similar criteria. Once the clinician has selected the desired patient, the clinician proceeds to step S506.

In step 506, once a patient is selected by the clinician, a drop down menu 218 is displayed for the patient including a list of the patient's available CT images 220 and any pathway plans 222 for the selected patient that have been previously created for each CT image 220. The clinician may choose to create a new plan based on the CT image 220 by selecting the create new plan option 224 and proceeding to step S510 or may open a previously created plan by selecting an open plan option 226 and proceeding to step S514, if a previously created plan is present for the selected CT image 220. When the create new plan option 224 is selected, the CT images 220 are imported, preferably in a DICOM format, into the pathway planning module 200. The computing device 100 processes the CT images 220 and assembles them into a three-dimensional CT volume by arranging the CT images 220 in the order they were taken and spacing them apart according a distance between slices set on the CT scanning device when they were taken. Pathway planning module 200 may perform a data fill function to create a seamless three-dimensional (3D) model or CT volume of the patient's bronchial tree. The pathway planning module 200 uses the newly-constructed CT volume to generate a three-dimensional map of the airways in the bronchial tree. The three dimensional map can either be skeletonized, such that each airway is represented as a line, or it may include airways having dimensions representative of their respective diameters. Preferably, when the three dimensional map is being generated, the airways are marked with an airflow direction (inhalation, exhalation, or separate arrows for each) for later use. Technologies for generating three-dimensional CT volumes and models are described in commonly assigned U.S. Pat. Nos. 6,246,784 and 6,345,112 both to Summers et al., as well as the references cited therein, all of which are hereby incorporated herein by reference.

Window 210 also includes a capture screen option 228 that allows the clinician to capture an image of the current screen shown on the display 102, for example, window 210, and save the captured image to memory. The capture screen option 228 may also be configured to remove patient specific data from the captured image to protect patient privacy. The removal of patient specific data may be an option selectable by the clinician and may be set to "on" by default.

Figure 6:
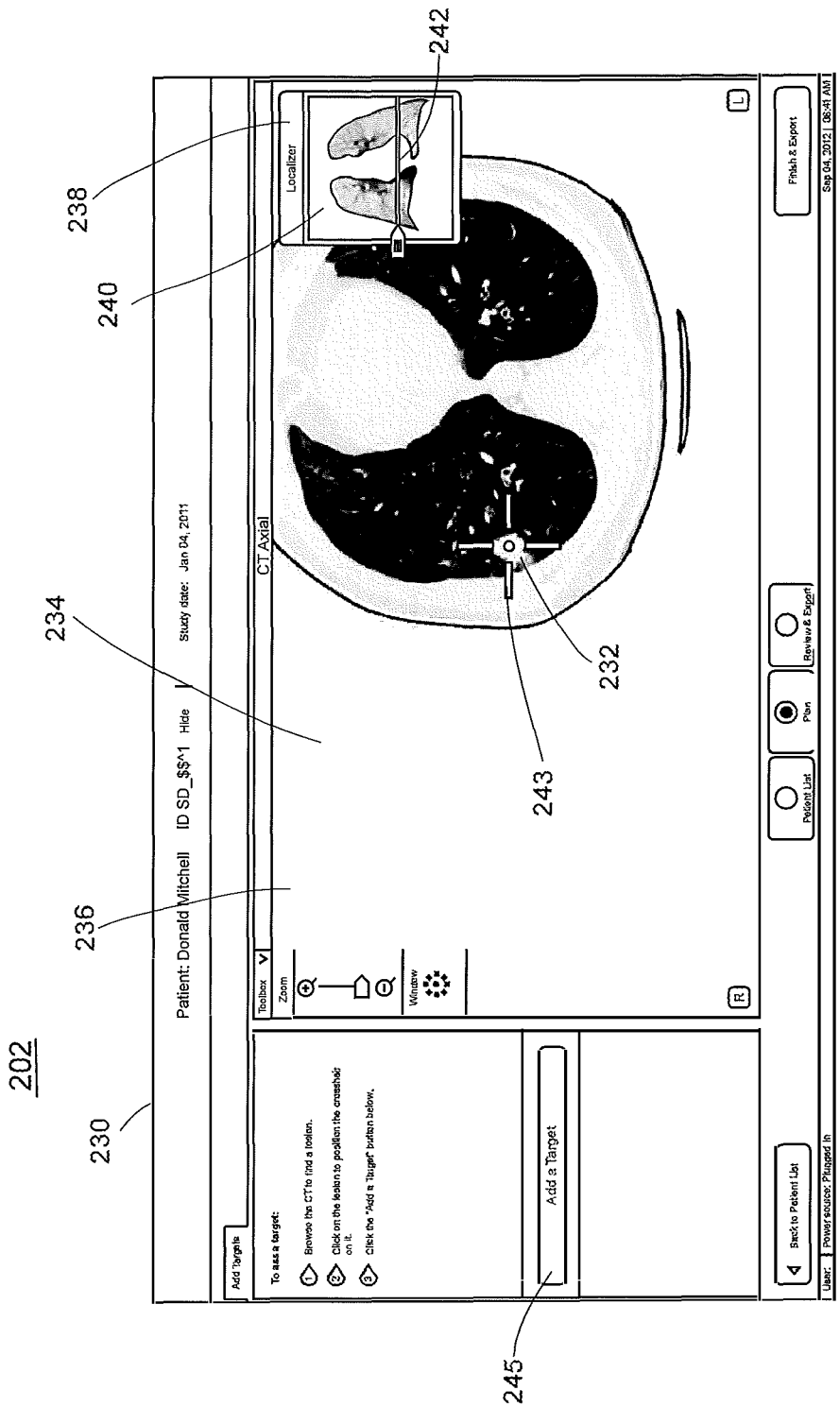
FIG. 6 is an illustration of a user interface for adding a target to a pathway plan in accordance with an embodiment of the present disclosure.
Figure 7:
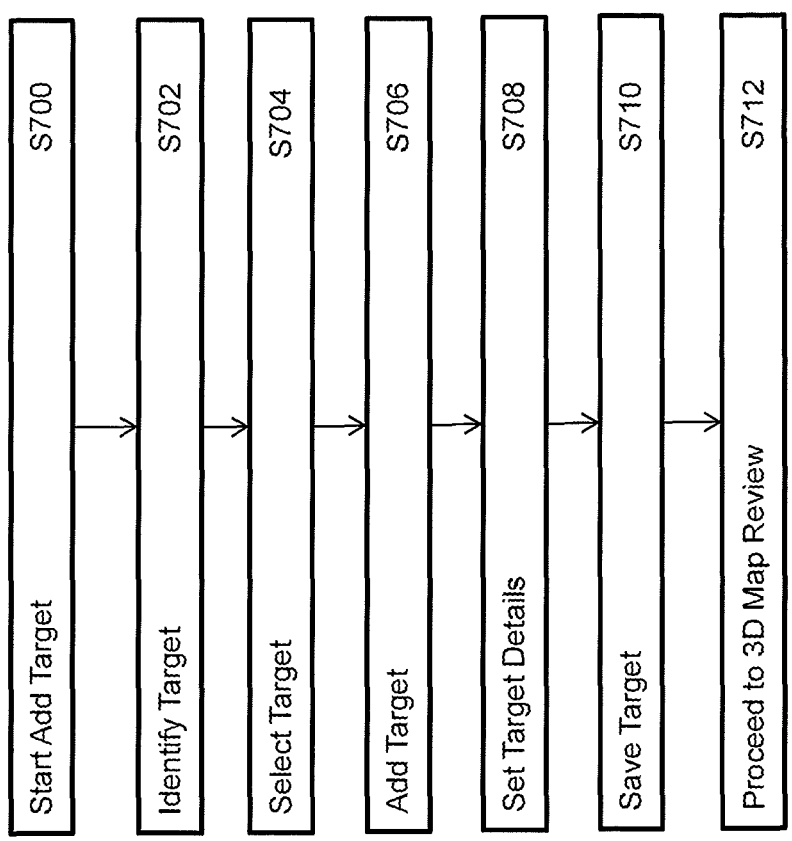
FIG. 7 is a flow chart of a method of adding a target to a pathway plan in accordance with an embodiment of the present disclosure.
Figure 8:
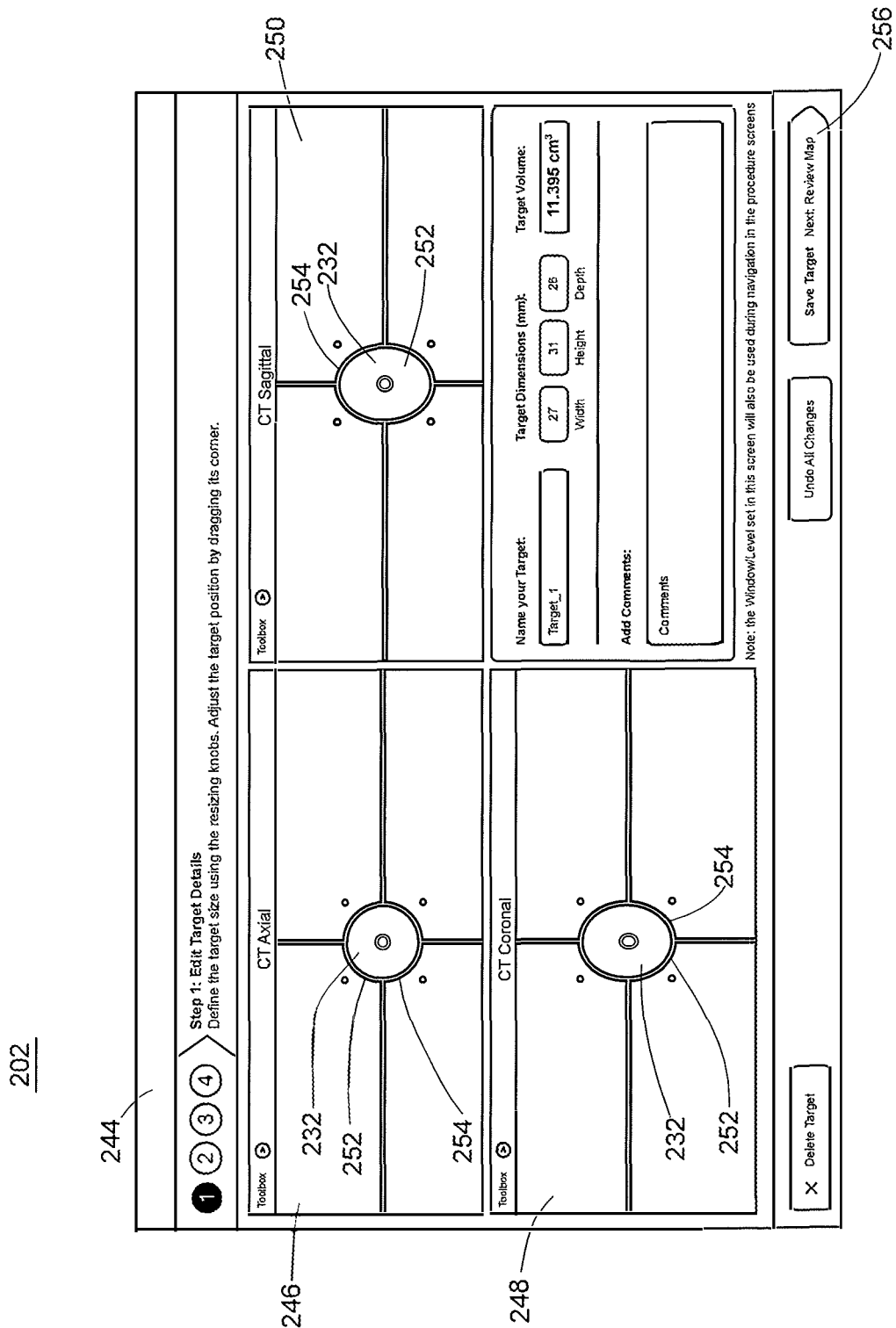
FIG. 8 is an illustration of a user interface for editing target details of an added target in accordance with an embodiment of the present disclosure.

Referring now to FIGS. 6-8, if the clinician has selected the create new plan option 224 from window 210, the method proceeds to step S512 and phase S2, adding a target. FIGS. 6 and 8 illustrate user interface 202 including windows 230 and 244 while FIG. 7 illustrates a method of adding a target according to an embodiment of the present disclosure. When phase S2 is initiated the method proceeds to step S700 and user interface 202 opens a window 230 for identification and selection of a target 232 on which to perform pathway planning. In window 230, the clinician is provided with a slice 234 of the CT image data in a main window 236. The slice 234 may be taken from the CT image data in any one of the Axial, Coronal and Sagittal directions. The clinician may freely switch the slice 234 shown in the main window 236 between slices 234 from the Axial, Coronal and Sagittal directions at any time. In the illustrated example, a slice 234 from the Axial CT image data is provided. It is important to note that by only showing a single slice and direction at a time, for example, only a slice 234 from the Axial CT image data, the clinician is provided with a simple and clean interface from which to select a target. The clinician may manipulate and relocate the image of the selected slice 234 in the main window 236 and may zoom in or out on the selected slice 234 to obtain an enlarged or reduced view of a particular portion of the selected slice 234.

Window 230 also includes a localizer 238 which provides a general overview of the patient's CT image data for use by the clinician. In the illustrated example, localizer 238 provides a localizer window 240 including generic view of a patient's lungs from the Coronal direction. The localizer window 240 may, for example, display a CT image from the Coronal direction, a fluoroscopy-like image, or other similar images that provide a clinician with a view of the patient's lungs. Localizer 238 includes a location element 242, for example, a line or bar, extending across localizer window 240 which provides a clinician with a location of the selected slice 234 displayed in main window 236 relative to the patient's lungs as displayed by the localizer 238. Location element 242 is selectable by the clinician and moveable or slidable relative to the localizer window 240 to allow the clinician to scroll through the CT image slices of the patient's lungs displayed on the main window 236. For example, the CT image slices may be scrolled through or displayed in a sequential order defined by the CT image data. The clinician may also or alternatively click on or select a portion of the localizer window 240 to move localizer 238 to the selected location in the patient's lungs. The clinician may also or alternatively scroll through the CT image slices of the patient's lungs displayed in the main window 236 via an input device such as, for example, a mouse wheel or other device without interacting directly with user interface 202. When another direction is selected for display on main window 236, for example, the Coronal direction, localizer 238 may display a generic view of one of the other directions, for example, the Axial or Sagittal direction. Localizer 238 provides the clinician with a general reference for where a particular lesion or other target 232 is located in the patient's lungs. Localizer 238 may also display one or more previously selected targets for the clinician's reference.

In step S702, the clinician scrolls through the CT image slices 234 to identify a target 232 on the CT image. In step S704, once a target 232 has been identified in the current CT slice 234, the clinician may click on or otherwise select the target 232 from the main window 236 using a target selection element 243, for example, a crosshair, mouse pointer, hand, or other similar selection element. The clinician may, for example, drag the CT image displayed on the main window 236 so that the target selection element 243 is positioned over the target 232, or alternatively, may directly select target 232 by clicking on the target 232 using a mouse (not shown) or other input device. If display 102 is touch-sensitive, the clinician may touch the target 232 on display 102 to select the target 232. The target 232 may then be added to the plan in step S706 by selecting the add a target option 245.

Referring now to FIG. 8, once a target 232 has been added, a target details window 244 is displayed by user interface 202. Target details window 244 may overlay window 230 or may replace window 230. Target details window 244 provides the clinician with the selected target 232 as shown in enlarged or zoomed versions of the Axial view 246, Coronal view 248 and Sagittal view 250. In step S708, the clinician may input width, height, and depth dimensions for the target 232, name the target 232, and add additional comments relating to the target 232. In addition, a target sizing element 252, e.g., a crosshair or other similar element, is positioned over the target 232 in each of views 246, 248, 250 and is manipulatable or movable by the clinician to center the target 232 in the target sizing element 252 in each view 246, 248, 250. Target sizing element 252 also includes an adjustable boundary ring 254 that is manipulatable by the clinician to resize the dimensions of the target 232. For example, the clinician may resize the boundary ring 254 on each of the Axial view 246, Coronal view 248 and Sagittal view 250 to accurately define the dimensions of the target 232. Boundary ring 254 may be circular, oval or other similar geometric shapes and the shape of the boundary ring 254 may be adjusted to substantially match the general dimensions of the target 232. In an embodiment, boundary ring 254 may be adjusted in a non-geometric manner by the clinician, for example, a free-form manipulation of boundary ring 254, to conform to non-geometric dimensions of the target 232. It is important to note that because the target 232 is a three dimensional object such as, for example, a lesion, tumor, or the like, and each view 246, 248, 250 is taken from a different direction, manipulation and adjustment of the boundary ring 254 on one of the views 246, 248, 250 by the clinician may result in a change or adjustment of the boundary ring 254 in one or both of the remaining views 246, 248, 250. In this manner the clinician may accurately select the target dimensions and the location of the target 232 in all three views, effectively mapping the target to specific coordinates and dimensions in a 3-D coordinate space. In step S710, once the dimensions and location of target 232 have been selected by the clinician the clinician selects the save target option 256 and proceeds to a review of the generated three dimensional map of the patient's bronchial tree in step S712.

Figure 9:
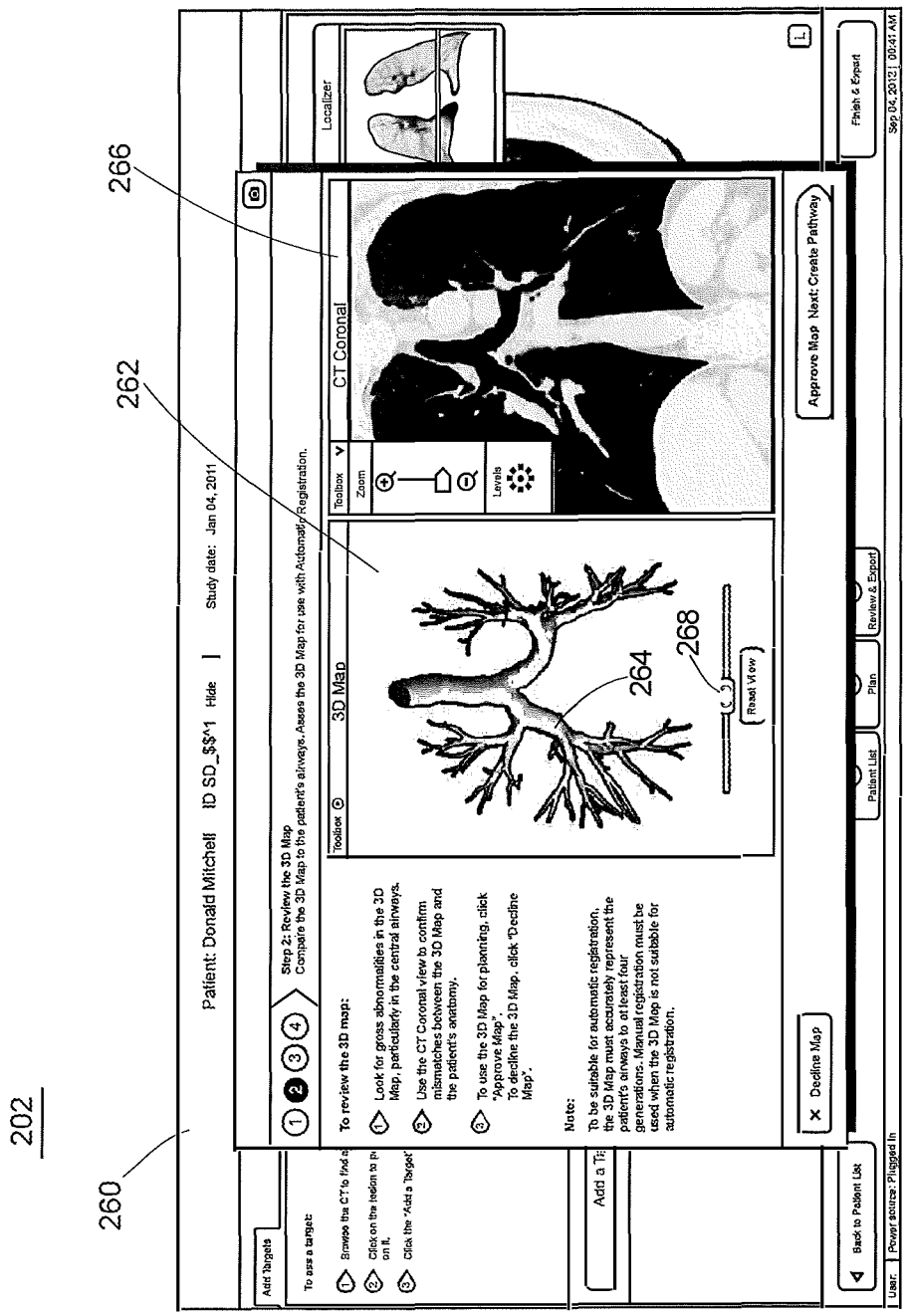
FIG. 9 is an illustration of a user interface for reviewing a 3D map in accordance with an embodiment of the present disclosure.
Figure 10:
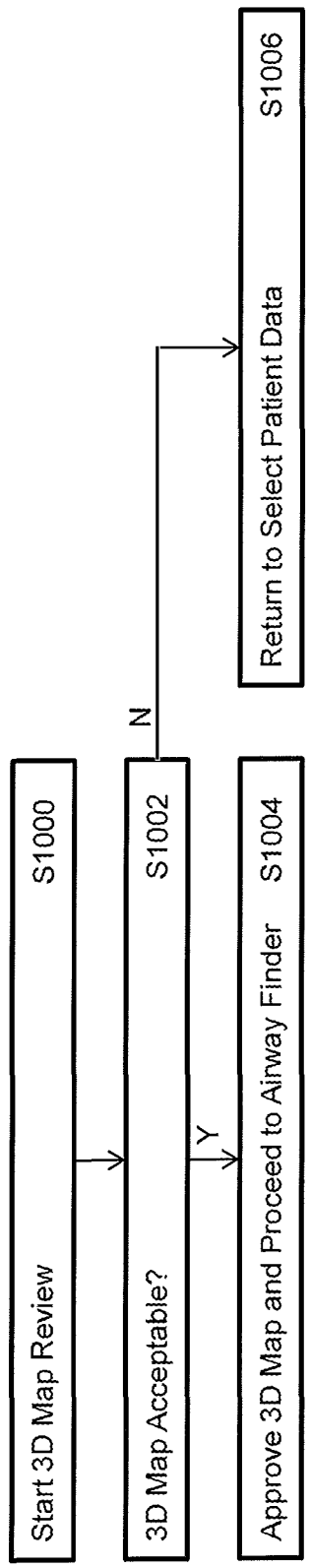
FIG. 10 is a flow chart of a method of reviewing a 3D map in accordance with an embodiment of the present disclosure.

Referring now to FIGS. 9 and 10, after the clinician has selected the save target option 256 of window 230, the method proceeds to step S1000, reviewing the 3D map of the bronchial tree. In step S1000, user interface 202 opens a window 260 for review of the three dimensional map generated by the pathway planning module 200. Window 260 includes a three dimensional map window 262 displaying a three dimensional model 264 of the patient's bronchial tree and a scan window 266 displaying a CT image from one of the Axial, Coronal and Sagittal directions for the clinician's reference. In the illustrated embodiment, the CT image from the Coronal direction is displayed. The CT image from the Coronal direction is displayed because the Coronal direction provides images of the patient's bronchial tree from the bird's eye or frontal view and is more likely to display to the clinician major recognizable features of the bronchial tree, for example, trunks and branches of the major airways. By comparing the CT image to the three dimensional model 264, the clinician is able to determine or verify that the three dimensional model 264 includes the major recognizable features of the patient's bronchial tree and also that there are no gross abnormalities in the three dimensional model 264 when compared to the CT image. In step S1002, the clinician rotates the three dimensional model as needed by manipulating a rotation slider 268 of three dimensional map window 262 to determine if the 3D map is acceptable. In step S1004, if the clinician is satisfied that the three dimensional model 264 is substantially accurate, for example, the major or central airways are sufficiently illustrated, the clinician selects the approve map option 270 and proceeds to the phase S3 and the airway finder. If the 3D map is not acceptable, the clinician proceeds to step S1006 and returns to step S500 to select new patient data, for example, a new patient or a new CT scan for the same patient.

Figure 11A:
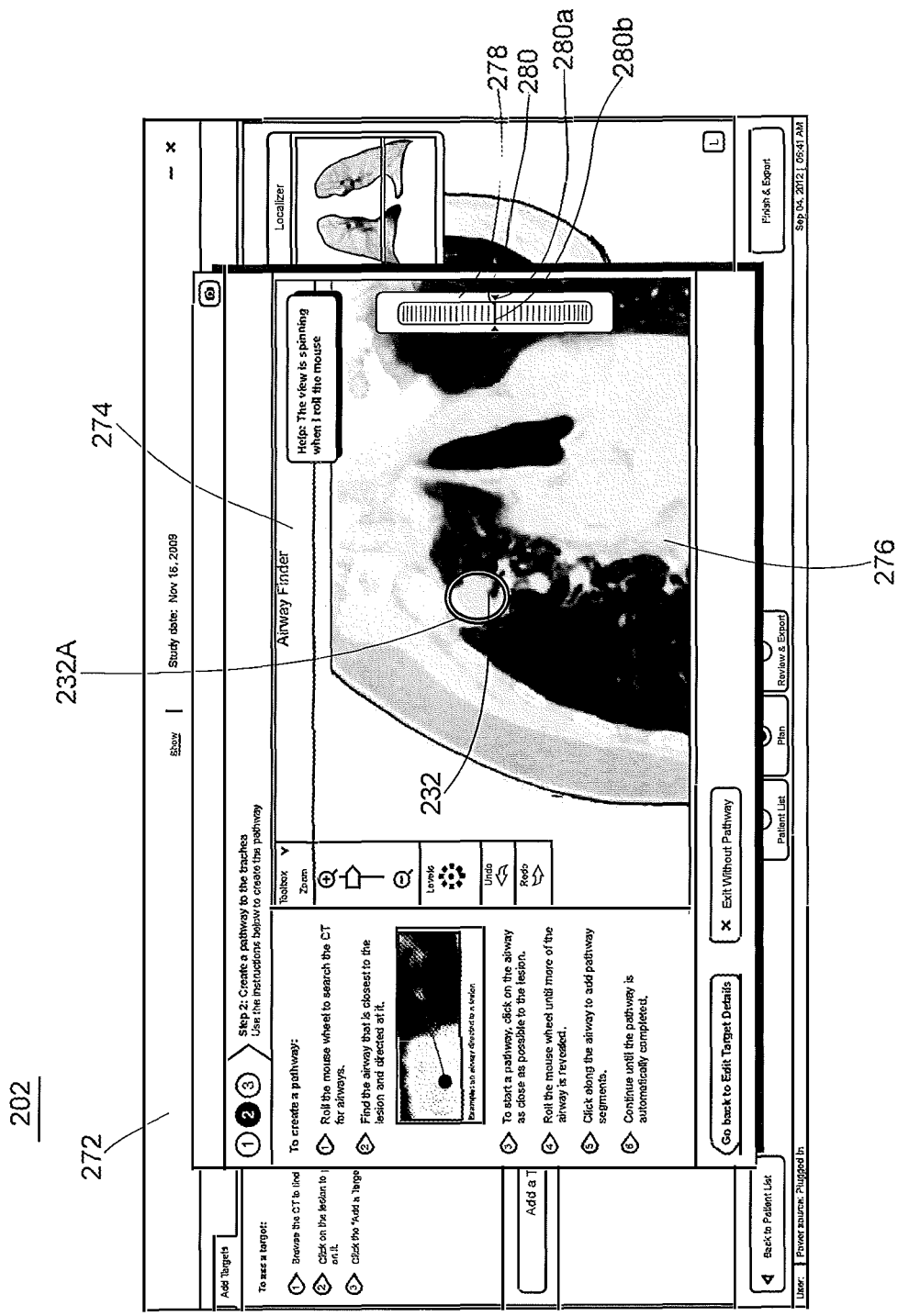
FIG. 11A is an illustration of a user interface for finding a pathway from a target to an entry point of a patient.
Figure 11B:
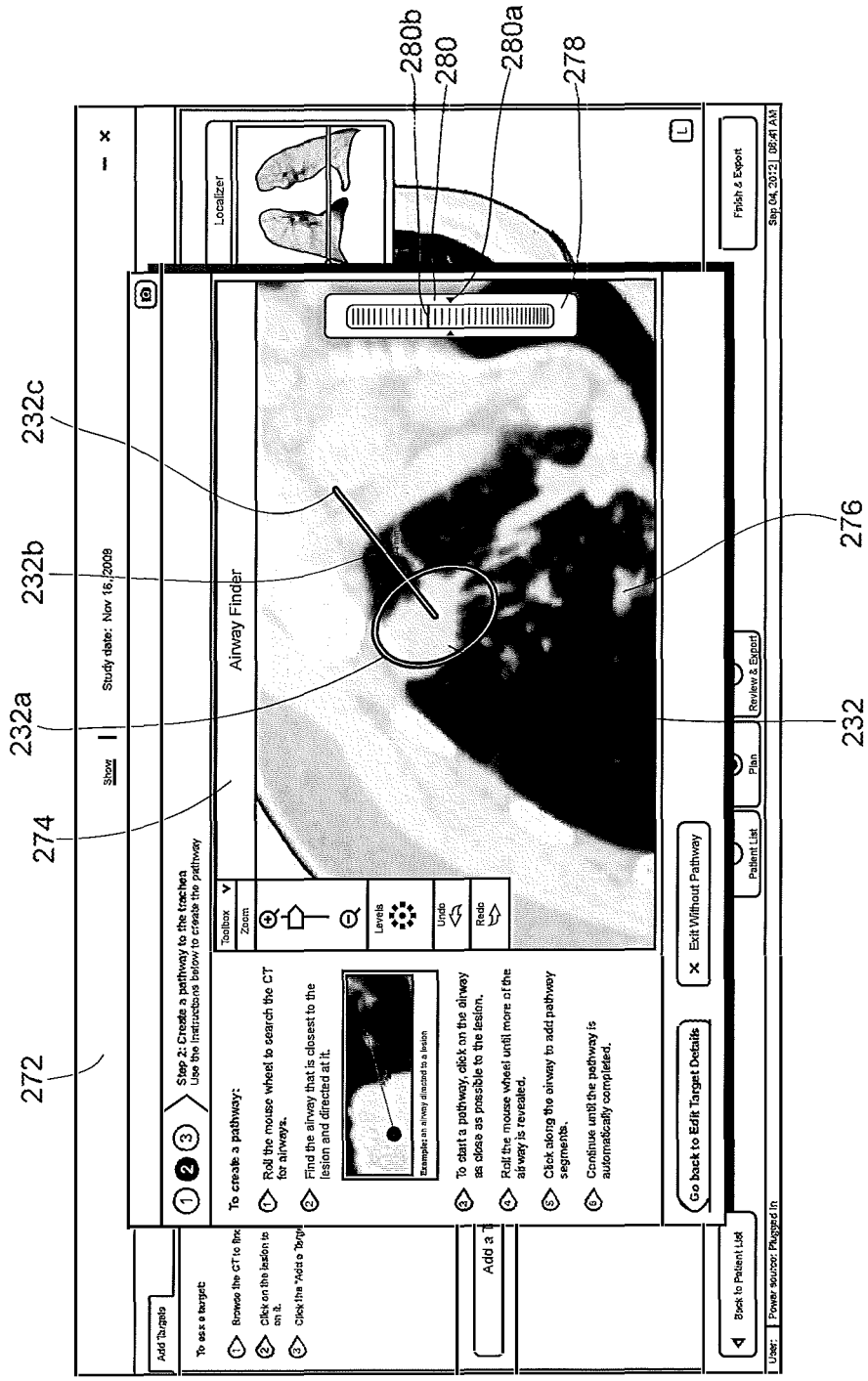
FIG. 11B is an illustration of the user interface of FIG. 11A after a CT image of the user interface has been rotated about an initial axis.
Figure 11C:
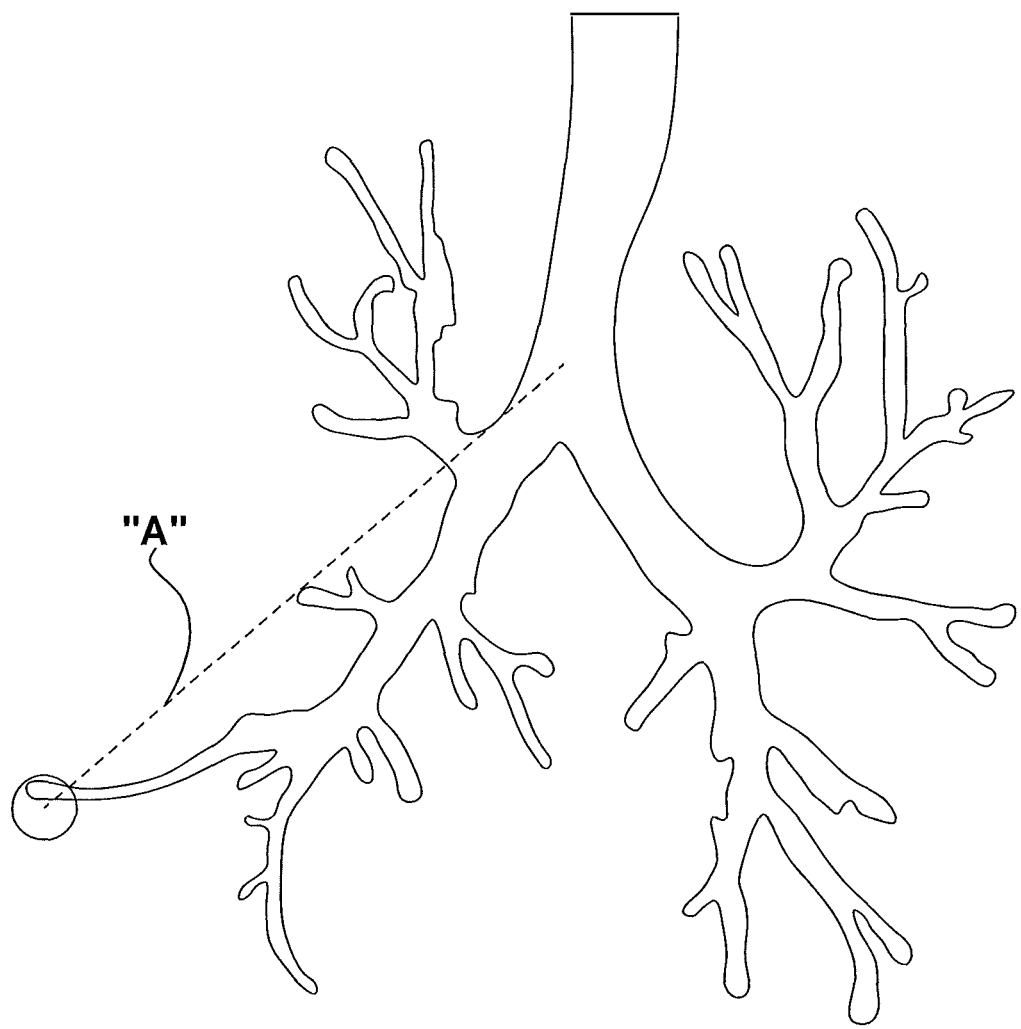
FIG. 11C is a perspective view of a 3D model of a patient's bronchial tree, illustrating an initial axis of rotation in accordance with an embodiment of the present disclosure.
Figure 11D:
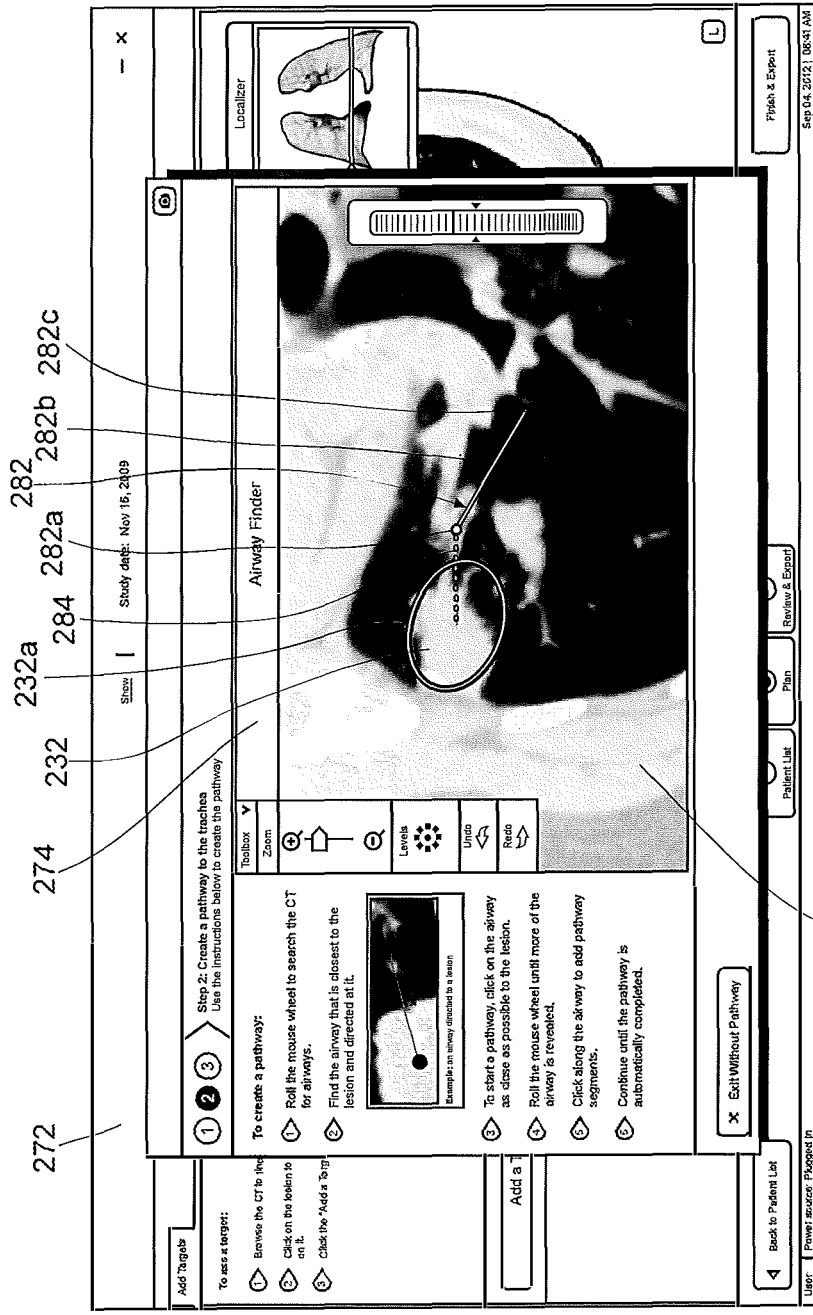
FIG. 11D is an illustration of the user interface of FIG. 11B after a waypoint has been added and a pathway between the target and the waypoint has been created with the CT image rotated about the axis of the pathway.
Figure 11E:
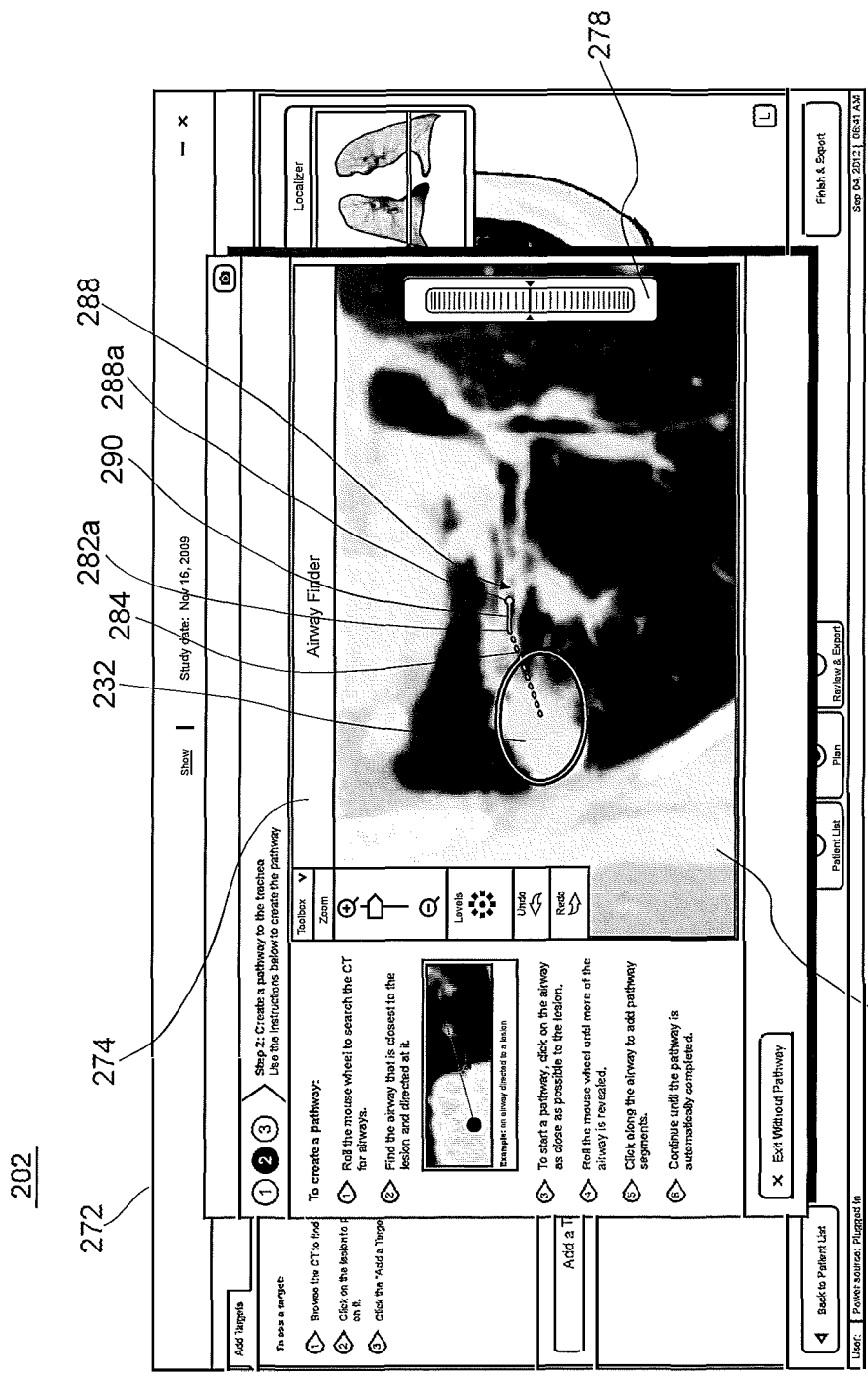
FIG. 11E is an illustration of the user interface of FIG. 11D after a second waypoint has been added and a second pathway between the waypoint and the second waypoint has been created.
Figure 11F:
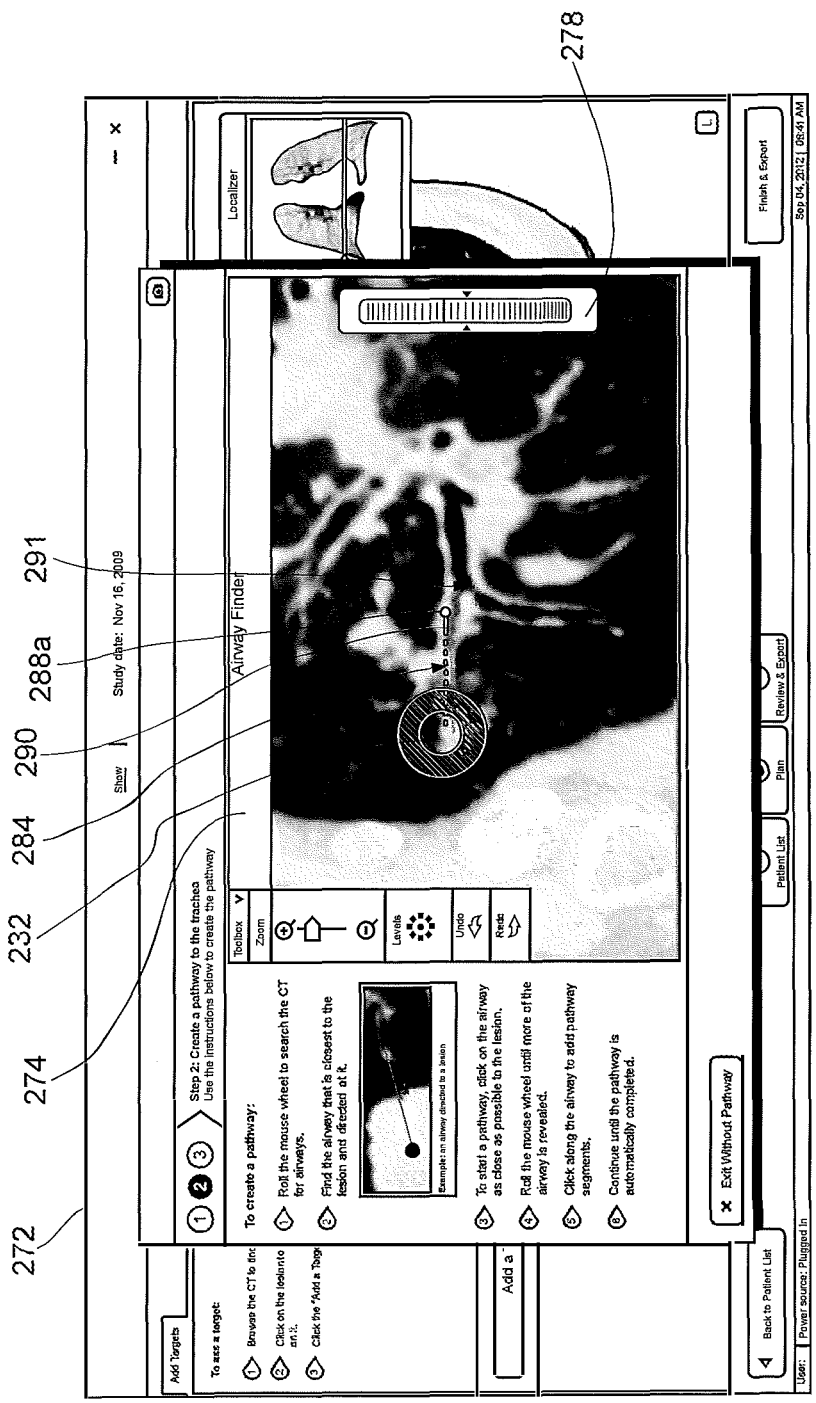
FIG. 11F is an illustration of the user interface of FIG. 11E after the CT image has been rotated about the axis of the second pathway to display a known airway.
Figure 11G:
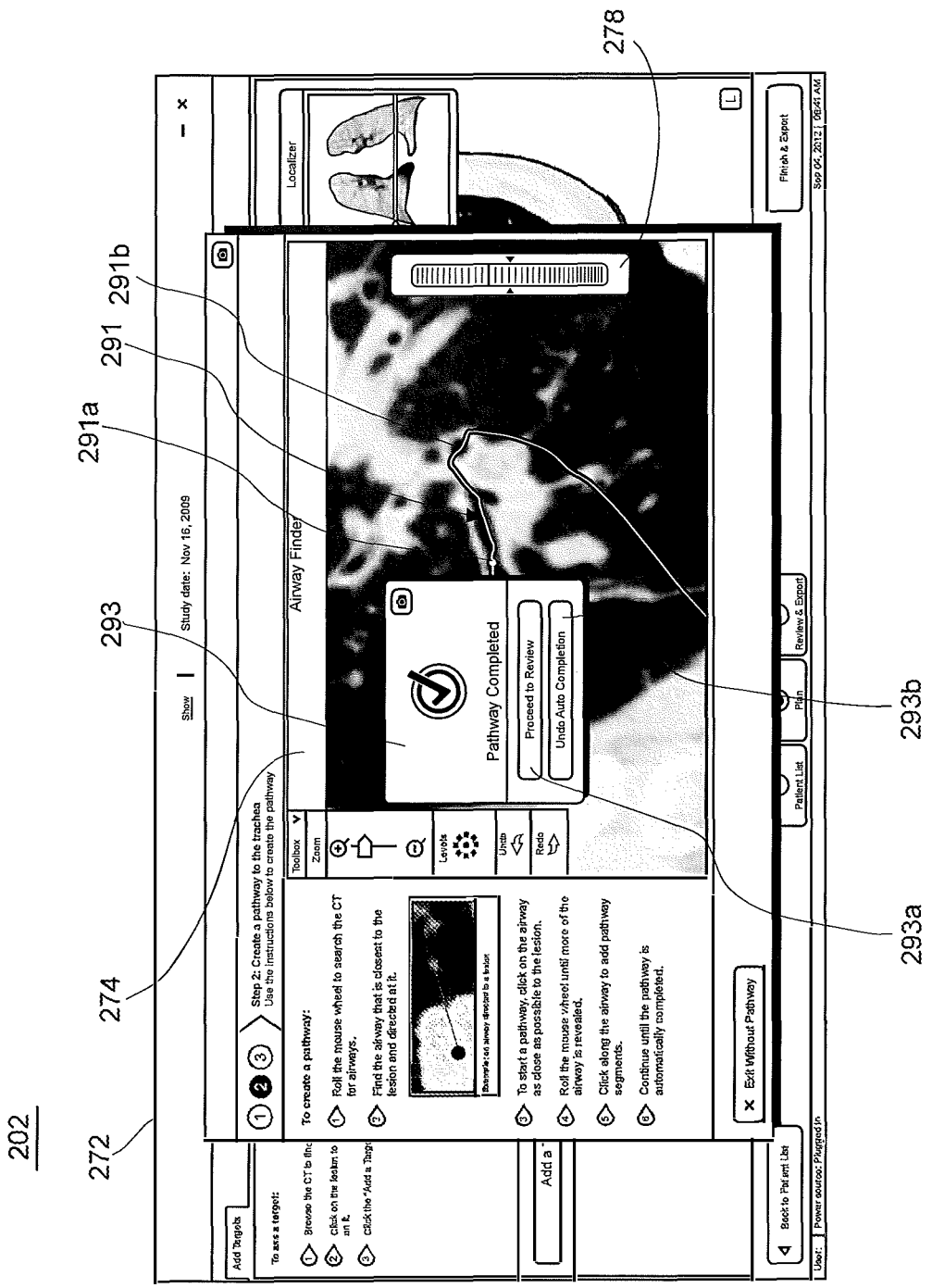
FIG. 11G is an illustration of the user interface of FIG. 11F after a third waypoint has been added within the known airway and the pathway has been automatically completed.
Figure 12:
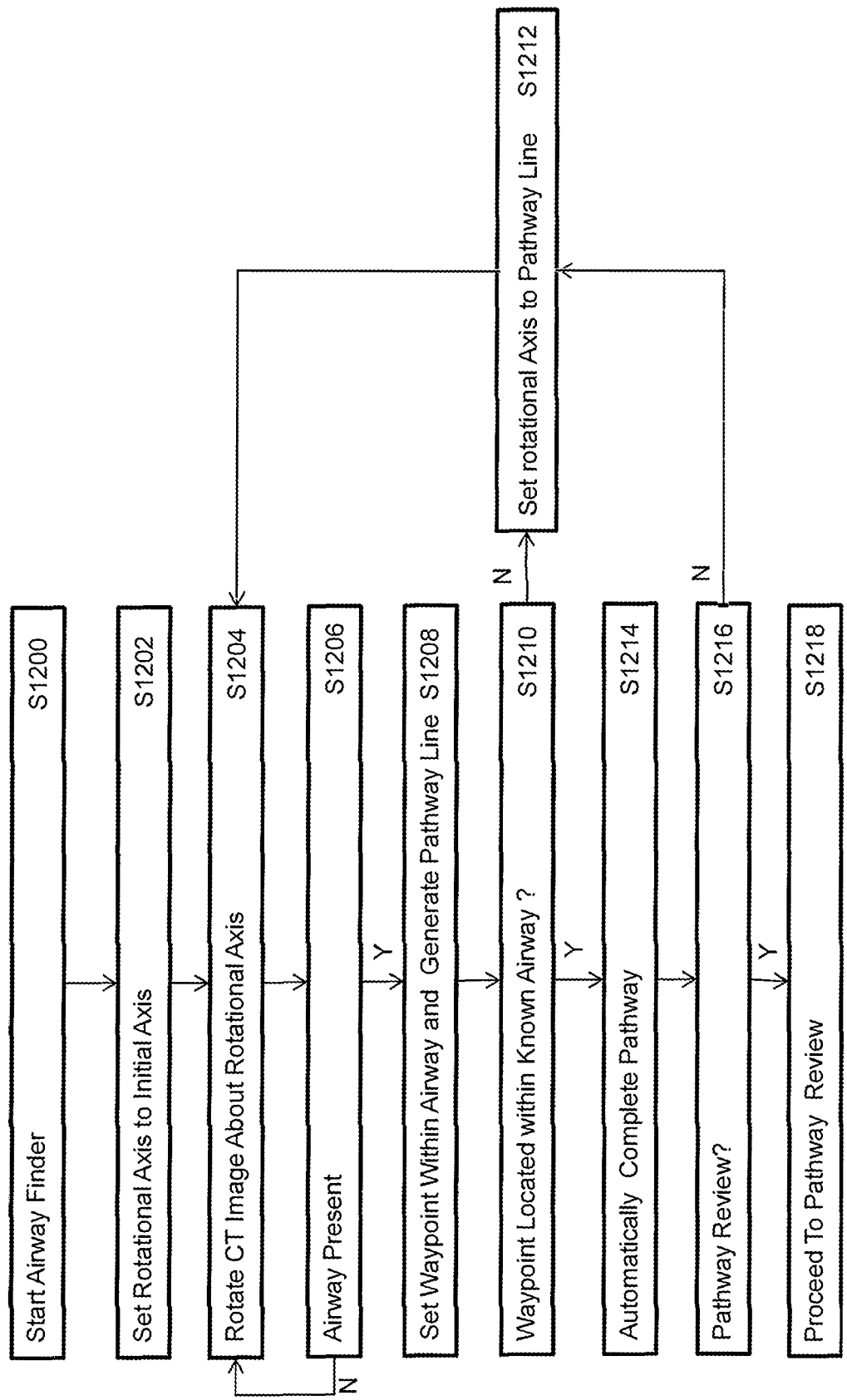
FIG. 12 is a flow chart of a method of finding a known airway and creating a pathway in accordance with an embodiment of the present disclosure.

Referring now to FIGS. 11A-11G and 12, after the clinician has selected the approve map option 270 of window 260, the method proceeds to phase S3 and step S1200 to start the airway finder. FIGS. 11A-11B and 11D-11G illustrate user interface 202 including window 272, FIG. 11C illustrates an initial axis "A" for use by the airway finder, and FIG. 12 illustrates a method of finding an airway and completing a pathway according to an embodiment of the present disclosure. In step S1200, referring initially to FIGS. 11A-11C, user interface 202 opens a window 272 for creating a pathway from the target 232 to the an entry point of the patient, for example, a natural orifice such as the mouth or nose, or an artificial entry point such as an incision. Window 272 includes an airway finder 274 displaying a CT image 276 including the target 232 and a rotation interface 278 describing the rotation of the CT image 276 about a specified axis. In an embodiment, upon initial opening of window 272, only the target 232 is shown on the CT image 276 of the airway finder window 274 and rotation indicators 280, e.g., arrows 280a and rotation bar 280b, on a rotation interface 278 are aligned. Rotation interface 278 provides rotational information regarding a relative rotation of CT image 276 about the specified axis. Referring now to FIG. 11B, a target marker 232A is displayed on the CT image 276 and is positioned over the target 232 to illustrate the location of target 232 to the clinician. A lead line 232B extends from a center of target marker 232A and is moveable by the clinician through movement of a pointer, mouse or other input devices. For example, the movement of an input device by the clinician moves an end 232C of lead line 232B that extends away from the target 232. The clinician uses lead line 232B to select an appropriate airway as will be described in more detail below with respect to step S1208.

In an embodiment, referring briefly to FIG. 11C, an initial axis "A" is set in step S1202 upon the initial opening of window 272 and is defined along an axis taken from the target 232 to a central portion of the tracheal lumen of the patient. By defining the initial axis "A" along axis from the target 232 to the trachea, the likelihood that a clinician can find an airway near the target 232 that will connect the target 232 to the entry point is increased. This is due to the tree like or branching nature of the bronchial tree. In other embodiments, the initial axis "A" may be defined along an axis taken from the target 232 to any other portion of the patient's bronchial tree, for example, to a central portion of the closest main branch of bronchial tree or to the closest known airway of the 3D map of the patient's bronchial tree.

In step S1204, the clinician rotates the CT image 276 about the initial axis by, for example, rolling a mouse wheel, manipulating another input device, and/or by manipulating a portion of user interface 202, for example, rotation interface 278. As the clinician rotates the CT image 276 about the initial axis, indicators 280 on the rotation interface 278 move relative to one another, for example, the rotation bar 280b moves relative to the arrows 280a, in a corresponding direction alone rotation interface 278 to indicate the amount of rotation relative to the initial view. When the rotation bar 280b reaches the end of rotation interface 278 after continued rotation in the same direction by the clinician, rotation bar 280b will disappear from the end of the rotation interface 278, reappear on an opposite end of rotation interface 278, and continue to slide along rotation interface 278 in the same direction. When the clinician has rotated the CT image 276 a full rotation about the initial axis, indicators 280, e.g., arrows 280a and rotation bar 280b, will once again be aligned at the center of rotation interface 278.

Referring now to FIGS. 11B and 11D, when rotating the CT image 276 about the initial axis, the clinician assesses the CT image 276 in step S1206 to determine whether an airway 282 near the target 232 is present. For example, an area of darkness in the CT image 276 that extends away from the target 232 or extends near the target 232 may be an indication that an airway 282 is present. If the clinician determines that an airway 282 is present, the method proceeds to step S1208 and the clinician positions end 232C of lead line 232B at the determined location within the airway 282 on the CT image 276 to create a pathway waypoint 282a on the CT image 276. The pathway planning module 200 draws a pathway line 284 between the target 232 and the pathway waypoint 282a on the CT image 276 and proceeds to step S1210. In this way, the clinician defines the portion of the airway 282 closest to the target 232. If no airway 282 is present, the clinician returns to step S1204 and continues to rotate the CT image about the specified axis. If the pathway waypoint 282a is not positioned correctly or the clinician desires to look for another airway, the clinician may remove the pathway waypoint 282a and return to either of steps S1204 or S1208.

In step S1210, pathway planning module 200 determines whether the pathway waypoint 282a selected by the clinician is located within a known airway of the three dimensional map generated by the pathway planning module 200. If the pathway waypoint 282a is located within a known airway of the three dimensional map, the method proceeds to step S1214 and the pathway is automatically completed by the pathway planning module 200 from the pathway waypoint 282a through the known airways of the three dimensional map to the trachea and the entry point of the patient, as further illustrated below for waypoint 282a in FIG. 11G.

If the pathway waypoint 282 is not located within a known airway of the three dimensional map, the method proceeds to step S1212. Referring now to FIGS. 11D and 11E, airway finder 274 displays a CT image 286 including the target 232, target marker 232a, pathway waypoint 282a, pathway line 284, and rotation interface 278, as described above. As illustrated in FIG. 11D, a lead line 282b having an end 282c now extends from pathway waypoint 282a.

In step S1212, the specified axis is set to an axis defined by pathway line 284. CT image 286 is rotatable about pathway line 284 instead of the initial axis "A" and rotation interface 278 displays the relative rotation of the CT image 286 about the axis defined by pathway line 284. By defining the axis of rotation about pathway line 284, the likelihood of the clinician finding airways on CT image 286 that connect to the airway 282 including the pathway waypoint 282a is increased. After the specified axis has been set to the axis of pathway line 284, the method returns to step S1204. When rotating the CT image 286 about the axis defined by pathway line 284, the clinician assesses the CT image 286 to determine whether an airway 288 connected to the pathway including pathway waypoint 282a is present as described above. If the clinician determines that an airway 288 is present in step S1206, the method proceeds to step S1208 and the clinician positions end 282C of lead line 282B at the determined location within the airway 288 on the CT image 286 to create a pathway waypoint 288a on the CT image 286. The pathway planning module 200 draws a pathway line 290 from pathway waypoint 282a to pathway waypoint 288a on the CT image 286, as illustrated in FIG. 11E. If the pathway waypoint 288a is not positioned correctly or the clinician desires to look for another airway, the clinician may remove the pathway waypoint 288a and return to either of steps S1204 or S1208.

In step S1210, referring now to FIGS. 11F, the pathway planning module 200 determines whether the pathway waypoint 288a selected by the clinician is located within a known airway, e.g., airway 291, of the three dimensional map generated by the pathway planning module 200. If the pathway waypoint 288a is not located within a known airway of the three dimensional map, the method proceeds to step S1212 and the clinician continues to set additional pathway waypoints as described above until a pathway waypoint is located within a known airway of the three dimensional map.

Referring now to FIG. 11G, a pathway waypoint 291a has been added in the manner described above in airway 291. In this illustration, airway 291 is a known airway of the three dimensional map. The method proceeds to step S1214 and the pathway 291b is automatically completed by the pathway planning module 200 from the pathway waypoint 291a through the airway 291 and the known branches of the three dimensional map of the bronchial tree to the entry point of the patient. Once a pathway is automatically completed, the method proceeds to step S1216 and a pathway completed window 292 is displayed by the user interface 202 providing the clinician with a proceed to pathway review option 293a and an undo automatic completion option 293a. The clinician may select the proceed to pathway review option 293a to proceed to step S1218 and start review of the pathway. Alternatively, if the clinician would like to continue mapping waypoints using airway finder 274, the clinician may select the undo automatic completion option 293b and return to step S1212 for the creation of further pathway waypoints as described above.

In this manner a pathway plan is created for later use by a clinician during a procedure or operation. Because the clinician can manually select and create the pathway and pathway waypoints that are closest to the target 232 prior to automatic completion, the clinician is able create a pathway plan that directly controls the final orientation of a medical device at the end of the pathway plan relative to the target 232. This allows the clinician to create a pathway plan for the medical device that will allow the medical device to travel along the small airways of the patient in a direction that will allow the working end of the medical device to be oriented generally toward the target 232, where generally toward the target 232 includes any orientation from which the clinician may effectively gain access to the target 232 within the limits of the medical device used.

Figure 13:
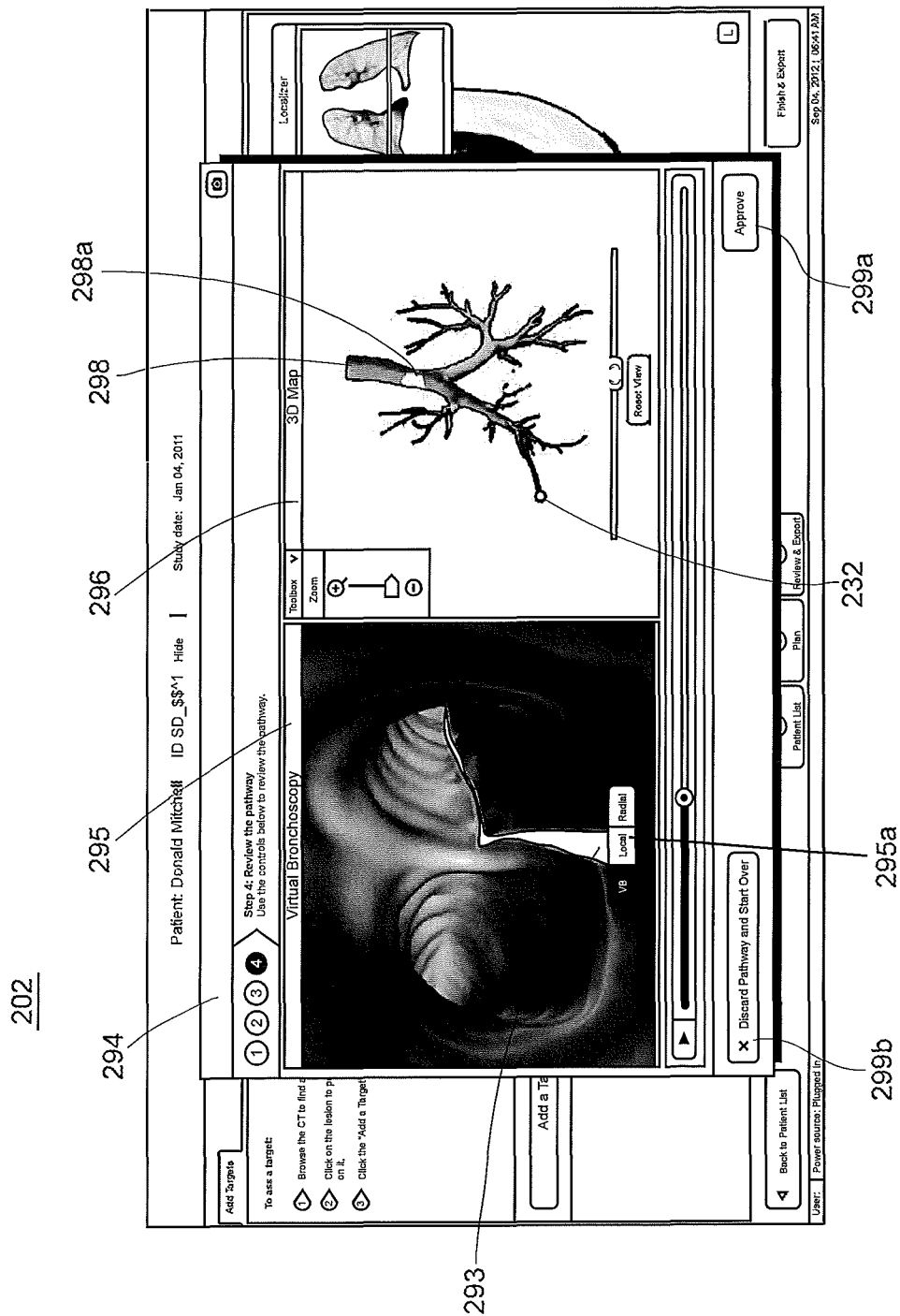
FIG. 13 is an illustration of a user interface for the reviewing a pathway accordance with an embodiment of the present disclosure.
Figure 14:
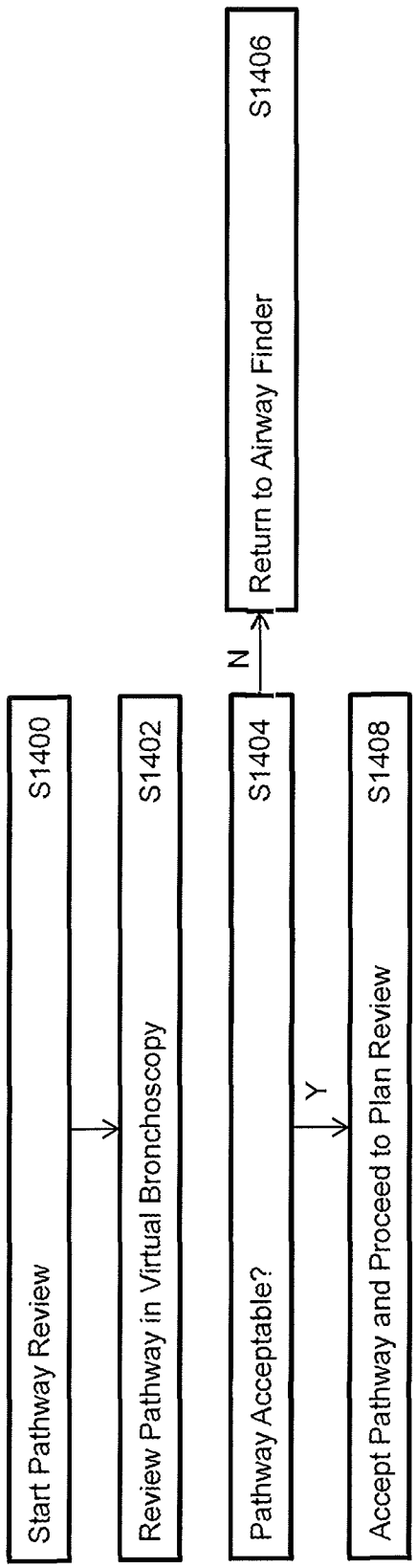
FIG. 14 is a flow chart of a method of reviewing a pathway in accordance with an embodiment of the present disclosure.

Referring now to FIGS. 13 and 14, after the clinician has completed a pathway, the method proceeds step S1400 and user interface 202 opens a window 294 for reviewing the pathway from the target 232 to the entry point of the patient. FIG. 13 illustrates user interface 202 including window 294 while FIG. 14 illustrates a method of reviewing a pathway according to an embodiment of the present disclosure. Window 294 includes a virtual window 295 and a three dimensional map window 296. Three dimensional map window 296 displays a three dimensional model 298 of the patient's bronchial tree similar to three dimensional map window 262. Virtual window 295 displays a CT-based "virtual bronchoscopy" which depicts simulated views similar to those of actual bronchoscope views and includes a view selection tab 295a for selecting between a virtual bronchoscopy view, a local view, and radial view. During the virtual bronchoscopy, the clinician may switch between the virtual, local and radial views as needed to review the pathway. The virtual bronchoscopy view displays a virtual visualization of the airways, derived from the CT data, that is an approximation of the video image from a bronchoscope, the local view displays an elevated perspective view of a cross-section of the CT volume through the current navigation location, and the radial view displays a cross-section of the CT volume that is perpendicular to the navigation location and local pathway segment. The technology of virtual bronchoscopy is described in commonly assigned U.S. Pat. Nos. 6,246,784 and 6,345,112 both to Summers et al., as well as the references cited therein, all of which are hereby incorporated herein by reference.

In step S1402, once the pathway has been created by the clinician, the user reviews the plan, targets and pathways by following a fly-through virtual bronchoscopy on virtual window 295. The user interface 202 generates a line 300 in virtual window 295 which represents the created pathway. The clinician follows the line 300 from the entry point through the trachea and through the airways of the patient's bronchial tree until the line 300 reaches the target 232. As can be appreciated, as the clinician follows the line 300 through the increasingly smaller airways of the patient's bronchial tree, the ability of the pathway planning module 200 to resolve the smaller airways is increasingly difficult due to a lack of resolution in the imported CT images. Because of this lack of resolution, the simulated views of the virtual bronchoscopy displayed in virtual window 295 may eventually fail to depict a clear airway lumen. Regardless, the target 232 and line 300 will be displayed in the virtual window 295 to allow the clinician to utilize the system for pathway planning purposes.

As the clinician follows the line 300 through the patient's bronchial tree to the target 232, a corresponding marker 298a travels along the three dimensional model 298 to the target 232 indicating a location of the simulated view of the virtual window 295 relative to the three dimensional model 298. In step S1404, after reviewing the virtual bronchoscopy the clinician determines whether the pathway is acceptable. If the pathway is acceptable the clinician may select the approve option 299a and the method proceeds to steps S1408. If the pathway is not acceptable, the method proceeds to steps S1406 and the clinician may select the discard pathway and start over option 299b to return to the airway finder window 272 to edit the pathway or create a new pathway.

Figure 15:
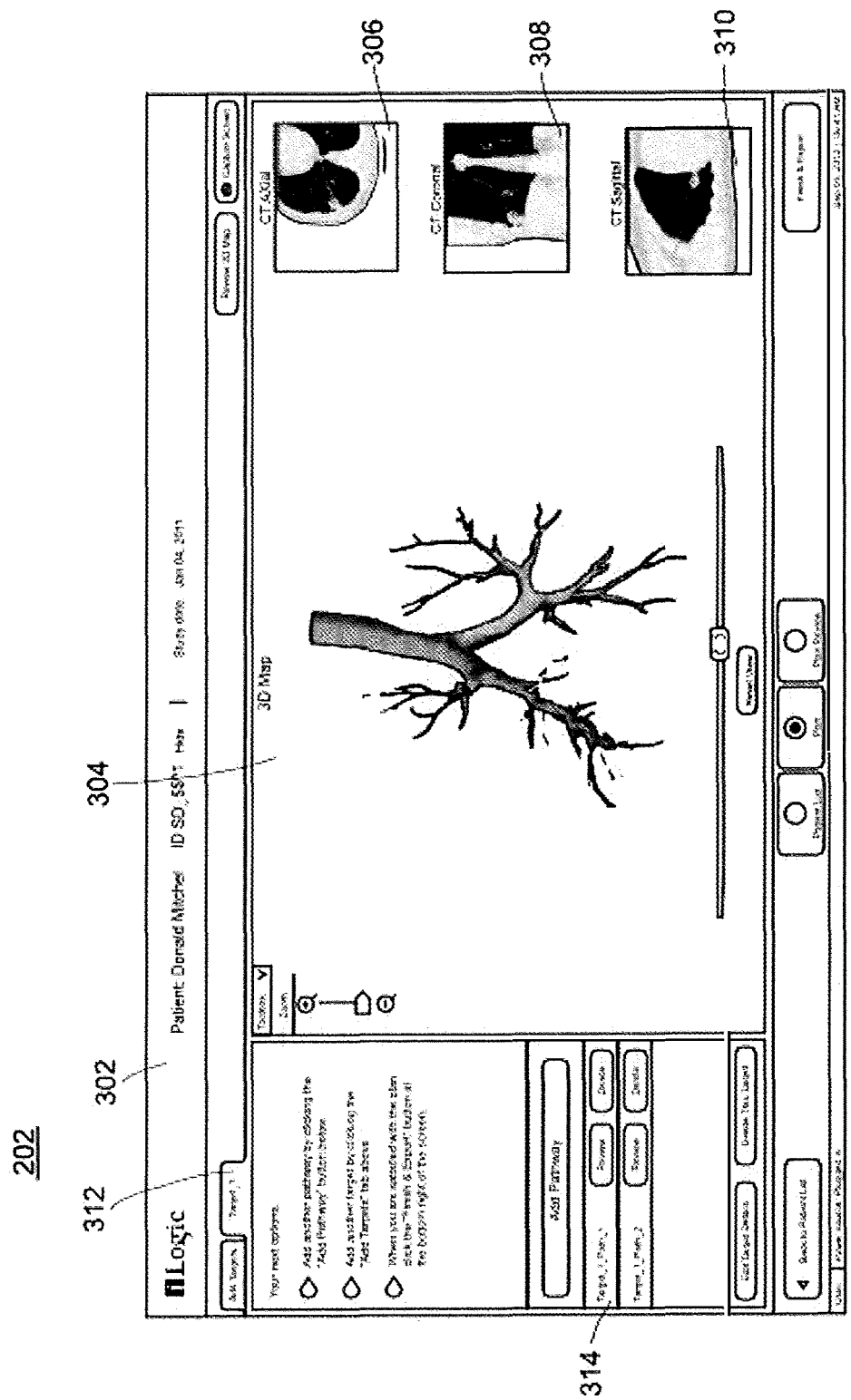
FIG. 15 is an illustration of a user interface for the reviewing a target and pathway and for creating additional targets and pathways in accordance with an embodiment of the present disclosure.
Figure 16:
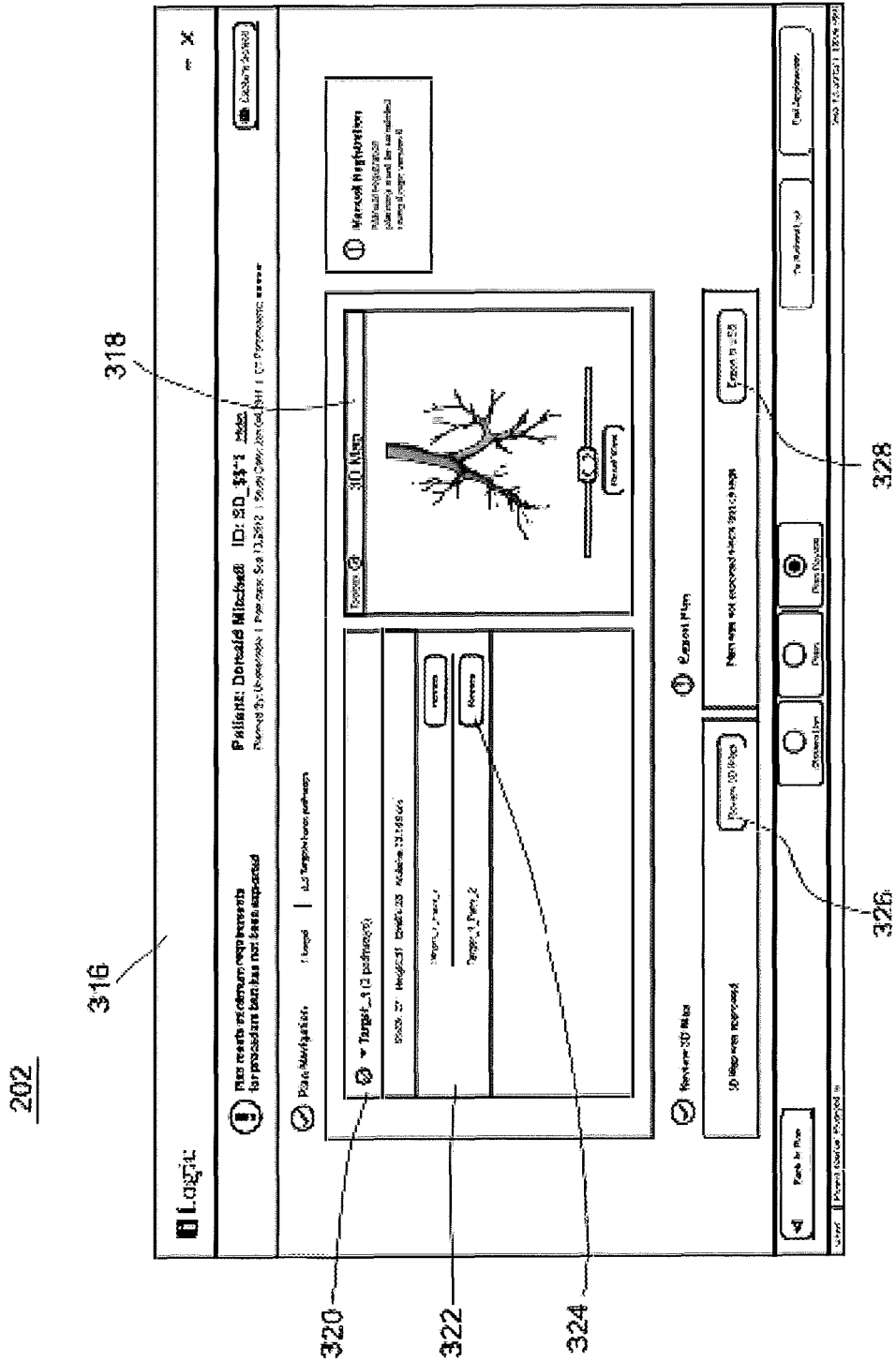
FIG. 16 is an illustration of a user interface for the reviewing and exporting a pathway plan in accordance with an embodiment of the present disclosure.
Figure 17:
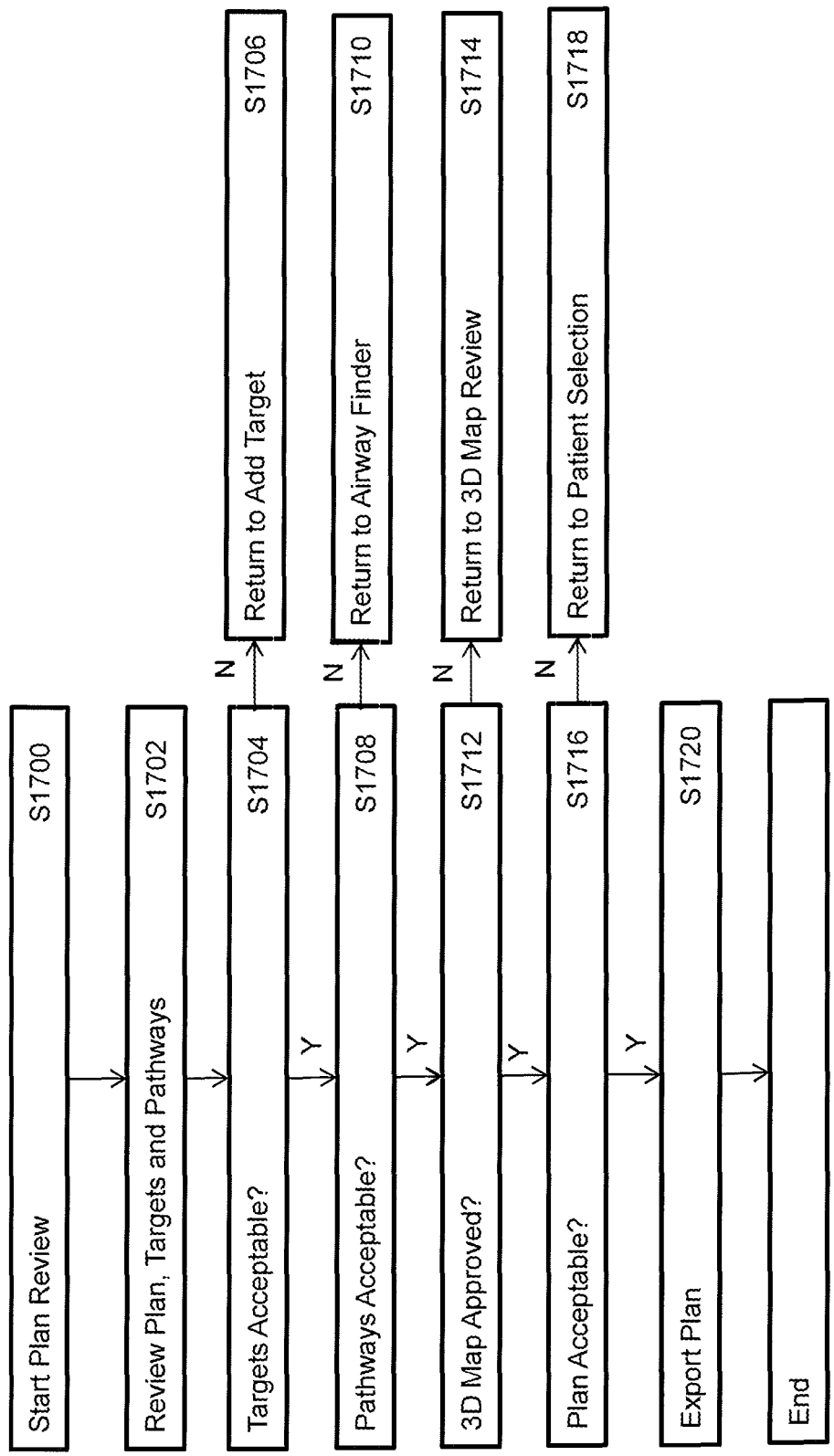
FIG. 17 is a flow chart of a method of reviewing and exporting targets, pathways, and pathway plans in accordance with an embodiment of the present disclosure.

Referring now to FIGS. 15-17, once the clinician has reviewed and accepted the pathway, the method proceeds to phase S4 and step S1700. FIGS. 15 and 16 illustrate user interface 202 including windows 302 and 316, respectively, while FIG. 17 illustrates a method of reviewing a plan according to an embodiment of the present disclosure. In step S1700, user interface 202 opens a window 302 including a three dimensional map window 304 and views of each of the Axial 306, Coronal 308 and Sagittal 310 directions displaying the selected pathway. Window 302 includes target tabs 312 and a pathway list 314. Target tabs 312 allow the clinician to add additional targets and select already identified targets for further review. Pathway list 312 allows the clinician to review the pathways associated with a selected target tab 312 and to add a pathway for the selected target tab 312. In step S1704, the clinician determines if the targets are acceptable. If the targets are not acceptable, the method proceeds to step S1706 and the pathway planning module 200 returns the clinician to the add a target window 230 to add a new target, as described above. If the targets are acceptable, the method proceeds to step S1708 and the clinician determines if the pathways are acceptable. If the pathways are not acceptable the method proceeds to step S1710 and the pathway planning module 200 returns the clinician to the airway finder window 272 for creation of additional pathways, as described above. If both the targets and the pathways are acceptable, the clinician selects the finish and export option 315 and proceeds to plan review in step S1716.

Referring now to FIG. 16, in step S1716 user interface 202 opens a window 316 including a three dimensional map window 318 and a list of the targets 320 identified for the selected plan. Each target 320 is selectable by the clinician to display the associated pathways 322 and each pathway 322 is reviewable by the clinician through the selection of a review option 324. Window 316 also provides an indication of whether the three dimensional map has been reviewed and approved and whether the current plan has been exported. In step S1712, if the 3D map has not been approved, the clinician may re-review the three dimensional map by selecting the review 3D map option 326. If the review 3D map option 326 has been selected, the method proceeds to step S1714 and the pathway planning module 200 returns the clinician to the review 3D map window 260 described above. If the 3D map has been approved, the method proceeds to step S1716 and the clinician determines whether the overall plan is acceptable. If the plan is not acceptable, the method proceeds to step S1718 and the pathway planning module 200 returns the clinician to the patient selection window 210 described above. If the clinician is satisfied with the plan, the method proceeds to step S1720 and the clinician may export the plan for use during a surgical procedure by selecting the export option 328. The plan may be exported to any form of non-transitory computer readable medium, memory or storage device as described above for memory 104 including, for example, a memory or storage on the device 100, a removable storage device, exported by transmission across a wired or wireless connection to a remote or server memory, etc.

With reference to FIGS. 4, 6, 15 and 16 the user interface 202 may include one or more navigation bars that are manipulatable by the clinician to return to or repeat any of the above phases and/or steps. For example, as illustrated in FIG. 4, the clinician may manipulate a navigation bar 330 to switch between the phases. The clinician may also be provided with the option to return to a previous step or window in any of the user interface 202 windows.

As noted above, the present disclosure employs CT images for the pathway planning. CT images are also typically used by the clinician during a medical procedure for the navigational purposes. The CT images are preferable to other imaging modalities because they have their own system of coordinates. Matching two systems of coordinates, e.g., that of the CT images and that of the patient, is commonly known as registration. Registration is generally performed by identifying locations in both the CT images and on or inside the body, and measuring their coordinates in both systems.

Methods of manual and semi-automated registration of CT data and patient data are described in detail in for example U.S. Pat. No. 7,233,820 assigned to Covidien LP and incorporated herein by reference. Because manual registration is somewhat time consuming and requires multiple steps, many practitioners rely on the automatic registration techniques described below. However, in some instances, particularly if the CT image data is not of sufficient quality it may still be necessary or desirable to conduct manual registration.

Automatic registration has become the norm for most procedures because while the manual fiducial point designation of the above referenced registration techniques is highly effective, the choice of number of points sampled necessarily represents a tradeoff between accuracy and efficiency. Similarly, while the semi-automated technique is a viable option it requires an image sensor at the distal end of the catheter assembly which adds increased complexity to the system.

Automatic registration techniques are described in detail in commonly assigned U.S. patent application Ser. No. 12/780,678, which is incorporated herein by reference in its entirety. Automatic registration between a digital image of a branched structure and a real-time indicator representing a location of a sensor inside the branched structure is achieved by using a sensor to "paint" a digital picture of the inside of the structure. Once enough location data has been collected, registration is achieved. The registration is "automatic" in the sense that navigation through the branched structure necessarily results in the collection of additional location data and, as a result, registration is continually refined.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method, for generating a pathway through a luminal network, comprising:
   receiving an indication of a target in a first two-dimensional image, the first two-dimensional (2D) image generated from a three-dimensional (3D) volume captured by an imaging device;
   depicting the target and at least a portion of the luminal network in a second 2D image, the second 2D image being generated from the 3D volume;
   rotating the 3D volume about an axis;
   updating the second 2D image;
   receiving an input identifying a first location of an airway; and
   generating a pathway through the luminal network to the target.

2. The method of claim 1, further comprising generating a 3D model of the luminal network from the 3D volume.

3. The method of claim 2, further comprising determining that the first location of the airway is outside of the 3D model of the luminal network.

4. The method of claim 3, wherein the axis is a first axis and the method further comprises rotating the 3D volume about a second axis defined by the target and the first location of the airway.

5. The method of claim 4, further comprising updating the second 2D image.

6. The method of claim 5, wherein the first location and a path line extending between the first location and the target, defining the second axis, is displayed on the updated second 2D image.

7. The method of claim 6, further comprising receiving an input identifying a second location of an airway.

8. A system for generating a pathway through a luminal network, the system comprising:
   a computing device including at least one processor and a computer-readable storage medium;
   a display device in communication with the computing device; and
   software, stored in the computer-readable storage medium and executable by the processor, wherein when executed the software:
      receives an indication of a target in a first two-dimensional image presented on the display, the first two-dimensional (2D) image generated from a three-dimensional (3D) volume captured by an imaging device;
      depicts the target and at least a portion of the luminal network in a second 2D image on the display, the second 2D image being generated from the 3D volume;
      receive an instruction to rotate the 3D volume about an axis;
      update the second 2D image presented on the display;
      receive an input identifying a first location of an airway; and
      generate a pathway through the luminal network to the target.

9. The system of claim 8, wherein when executed the software generates a 3D model of the luminal network from the 3D volume.

10. The system of claim 9, wherein when executed the software determines that the first location of the airway is outside of the 3D model of the luminal network.

11. The system of claim 10, wherein the axis is a first axis and the method when executed the software receives an input to rotate the 3D volume about a second axis defined by the target and the first location of the airway.

12. The system of claim 11, wherein when executed the software updates the second 2D image.

13. The system of claim 12, wherein when executed the software displays on the updated second 2D image the first location and a path line extending between the first location and the target, defining the second axis.

14. The system of claim 13, wherein when executed the software receives an input identifying a second location of an airway.

15. A non-transitory computer-readable storage medium encoded with a program for generating a pathway through a luminal network that, when executed by a processor performs the steps of:

receiving an indication of a target in a first two-dimensional image, the first two-dimensional (2D) image generated from a three-dimensional (3D) volume captured by an imaging device;

depicting the target and at least a portion of the luminal network in a second 2D image, the second 2D image being generated from the 3D volume;

rotating the 3D volume about an axis;

updating the second 2D image;

receiving an input identifying a first location of an airway; and generating a pathway through the luminal network to the target.

16. The non-transitory computer-readable storage medium according to claim 15, further performing a step of generating a 3D model of the luminal network from the 3D volume.

17. The non-transitory computer-readable storage medium according to claim 16, further performing a step of determining that the first location of the airway is outside of the 3D model of the luminal network.

18. The non-transitory computer-readable storage medium according to claim 17, wherein the axis is a first axis and the method further comprises performing a step of rotating the 3D volume about a second axis defined by the target and the first location of the airway.

19. The non-transitory computer-readable storage medium according to claim 18, further performing a step of updating the second 2D image.

20. The non-transitory computer-readable storage medium according to claim 19 further performing a step of displaying on the updated second 2D image the first location and a path line extending between the first location and the target, defining the second axis.

* * * * *